（12）United States Patent
Ruffini et al.

(10) Patent No.: US 11,479,605 B2
(45) Date of Patent: Oct. 25, 2022

(54) HOMODIMERIC PROTEIN CONSTRUCTS

(71) Applicant: Nykode Therapeutics ASA, Oslo (NO)

(72) Inventors: Pier Adelchi Ruffini, Milan (IT);
Bjarne Bogen, Snaroya (NO); Agnete Brunsvik Fredriksen, Raelingen (NO)

(73) Assignee: Nykode Therapeutics ASA, Oslo (NO)

( * ) Notice: Subject to any disclaimer, the term of this patent is extended or adjusted under 35 U.S.C. 154(b) by 58 days.

(21) Appl. No.: 16/784,778

(22) Filed: Feb. 7, 2020

(65) Prior Publication Data

US 2020/0239568 A1 Jul. 30, 2020

Related U.S. Application Data

(62) Division of application No. 13/805,709, filed as application No. PCT/EP2011/060628 on Jun. 24, 2011, now Pat. No. 10,590,195.

(60) Provisional application No. 61/358,513, filed on Jun. 25, 2010.

(30) Foreign Application Priority Data

Jun. 25, 2010 (EP) .................................. 10167291

(51) Int. Cl.
*C07K 16/28* (2006.01)
*A61K 39/00* (2006.01)
*C07K 16/44* (2006.01)
*A61K 39/145* (2006.01)
*A61K 39/12* (2006.01)

(52) U.S. Cl.
CPC .......... *C07K 16/28* (2013.01); *A61K 39/0011* (2013.01); *A61K 39/00119* (2018.08); *A61K 39/001157* (2018.08); *A61K 39/001194* (2018.08); *A61K 39/12* (2013.01); *A61K 39/145* (2013.01); *C07K 16/44* (2013.01); *A61K 2039/53* (2013.01); *A61K 2039/54* (2013.01); *A61K 2039/6031* (2013.01); *A61K 2039/6056* (2013.01); *C07K 2317/526* (2013.01); *C07K 2317/53* (2013.01); *C07K 2317/622* (2013.01); *C07K 2317/64* (2013.01); *C07K 2319/30* (2013.01); *C07K 2319/33* (2013.01); *C07K 2319/40* (2013.01); *C07K 2319/42* (2013.01); *C12N 2760/16111* (2013.01); *C12N 2760/16134* (2013.01)

(58) Field of Classification Search
None
See application file for complete search history.

(56) References Cited

U.S. PATENT DOCUMENTS 5,580,859 A 12/1996 Feigner et al.
5,646,016 A 7/1997 McCoy et al.
6,099,846 A 8/2000 Levy et al.
2003/0100497 A1 5/2003 Baker et al.
2004/0253238 A1* 12/2004 Bogen .................. C12N 9/1276
424/144.1
2005/0069549 A1 3/2005 Herman
2006/0165713 A1 7/2006 Gough et al.
2007/0065444 A1 3/2007 North et al.
2007/0298051 A1 12/2007 Barouch et al.
2009/0010948 A1 1/2009 Huang et al.
2009/0092578 A1* 4/2009 Su ....................... C07K 16/1203
424/85.2
2011/0263835 A1 10/2011 Ting et al.

FOREIGN PATENT DOCUMENTS

| EP | 920522 | 2/1998 |
|---|---|---|
| JP | 2013-532971 | 8/2013 |
| WO | WO 92/13955 | 8/1992 |
| WO | WO 00/15663 A1 | 3/2000 |
| WO | WO 03/05992 A1 | 7/2003 |
| WO | WO 2003/059951 | 7/2003 |
| WO | WO 2004/076489 | 9/2004 |
| WO | WO 2011/161244 A1 | 12/2011 |

OTHER PUBLICATIONS

Fredriksen and Bogen (Blood, 110: 1797-1805, 2007).*
Rahman et al. (Hepatology, 31: 521-521, 2000).*
Biragyn, Aiya et al., "Genetic fusion of chemokines to a self tumor antigen induces protective, T-cell dependent antitumor immunity" Nature Biotechnology, 1999, pp. 253-258, vol. 17.
Biragyn, Aiya et al., "Toll-Like Receptor 4-Dependent Activation of Dendritic Cells by Beta-Defensin 2" Science, 2002, pp. 1025-1029, vol. 298.
Bogen, B., et al., "Weak positive selection of transgenic T cell receptor-bearing thymocytes: importance of major histocompatibility complex class II, T cell receptor and CD4 surface molecule densities," *European Journal of Immunology*, 1992 pp. 703-709, vol. 22.
Borysiewicz, L., et al., "A recombinant vaccinia virus encoding human papillomavirus types 16 and 18, E6 and E7 proteins as immunotherapy for cervical cancer," *The Lancet*, 1996, vol. 347, pp. 1523-1527.
Brunsvik, A et al., "Construction ofTetrabodies for Cancer Vaccines" The National Hospital, Oslo, NO, Abstract, 2002.
Brunsvik, A. et al., "Vaccibodies: Future Vaccines for B Cell Lymphoma and Myeloma?" Institute of Immunology, Univ. of Oslo, Oslo National Hospital; Oslo, NO, Abstract, 2003.

(Continued)

*Primary Examiner* — Nelson B Moseley, II
(74) *Attorney, Agent, or Firm* — Womble Bond Dickinson (US) LLP

(57) ABSTRACT

The present invention relates to novel recombinant fusion proteins, such as human antibody-based molecules called Vaccibodies, which are able to trigger both a T cell- and B cell immune response. The present invention also relates to a method of treating a cancer or an infectious disease by means of these specific fusion proteins.

19 Claims, 8 Drawing Sheets

Figure 1:
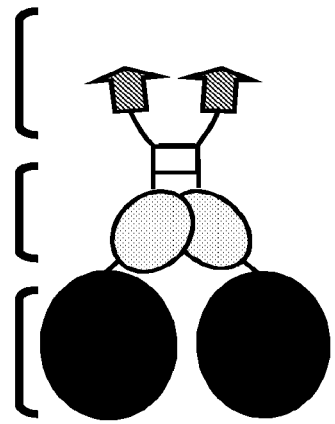
Figure 1:
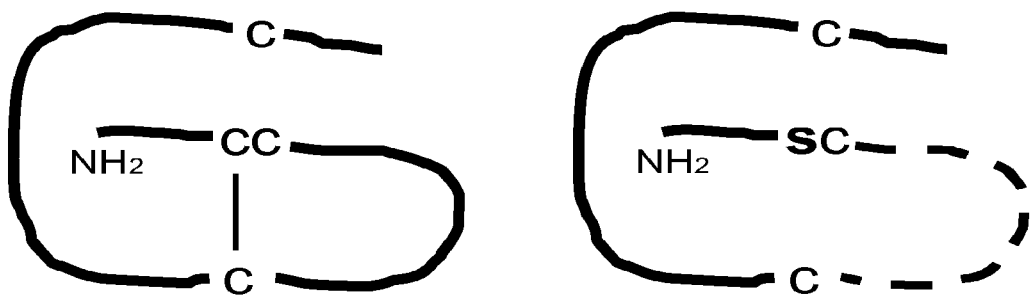

Specification includes a Sequence Listing.

(56) References Cited

OTHER PUBLICATIONS

Chen, Hsin-Wei et al., "Linkage of CD40L to a self-tumor antigen enhances the antitumor immune responses of dendritic cell-based treatment" Cancer Immunol Immunother, 2002, pp. 341-348, vol. 51.

Dennis, Carina, "Off by a whisker" Nature, 2006, pp. 739-741, vol. 442.

Eisen, Herman N. et al., "Lambda Chains and Genes in Inbred Mice" Annual Reviews Immunology, 1985, pp. 337-365 vol. 3.

Eisen, Herman N. et al., "Mouse Myeloma Proteins with Antihapten Antibody Activity. The Protein Produced by Plasma Cell Tumor MOPC-315" Biochemistry, 1968, pp. 4126-4134, vol. 7, No. 1.

Fredriksen, Agnete Brunsvik et al., "DNA Vaccines Increase Immunogenicity of Idiotypic Tumor Antigen by Targeting Novel Fusion Proteins to Antigen-Presenting Cells" Molecular Therapy, 2006, pp. 776-785, vol. 13

Fredriksen, Agnete Brunsvik and Bogen, Bjarne, "Chemokine-idiotype Fusion DNA Vaccines are Potentiated by Bivalency and Xenogeneic Sequences" Blood, 2007, pp. 1797-1805, vol. 110.

Hoogenboom, Rennie R.; "Mix and match: Building manifold binding sites" Nature Biotechnology, 1997, pp. 125-226, vol. 15.

Horwell, D. C., "The peptoid approach to the design of non-peptide, small molecule agonists and antagonists of neuropeptides," *Trends in Biotechnology*, 1995, pp. 132-134, vol. 13(4).

Hu, Shi-zhen et al., "Minibody: A Novel Engineered Anti-Carcinoembryotic Antigen Antibody Fragment (Single-Chain Fv-CH3), Which Exhibits Rapid, High-Level Targeting of Xenografts" Cancer Research, 1996, pp. 3055-3061, vol. 56.

Huang, Hsing-I et al., "Improved immunogenicity of a self tumor antigen by covalent linkage to CD40 ligand" International Journal of Cancer, 2004, pp. 696-703, vol. 108.

Huang, Tzu-Hsuan et al., "Enhanced anti tumor immunity by fusion of CTLA-4 to a self tumor antigen" Blood, 2000, pp. 3663-3670, vol. 96, No. 12.

Kriangkum, J., et al., "Bispecific and bifunctional single chain recombinant antibodies," Biomolecular.Engineering,.2001, pp. 31.-40, vol. 18(2).

Kutzler, M. A., and Weiner, D. B., "DNA Vaccines: Ready for Prime Time?" *Nature Reviews: Genetics*, 2008, pp. 776,788, vol. 9(10).

Lewis, Anne D. et al., "Generation of Neutralizing Activity against Human Immunodeficiency Virus Type 1 in Serum by Antibody Gene Transfer" Journal of Virology, 2002, pp. 8769-8775, vol. 76, No. 17.

Lunde E, et al., "Troybodies and Pepbodies" Biochemical Society Transactions, 2002, pp. 500-506, vol. 30, part 4.

Lunde, Elin et al., "'Troy-bodies': Recombinant Antibodies that Target T Cell Epitopes to Antigen Presenting Cells" International Reviews of Immunology, 2001, pp. 647-673, vol. 20.

Macgregor, R. R., et al., "T-cell responses induced in normal volunteers immunized with a DNA-based vaccine containing IIIV-1 env and rev," Aids, 2002, pp. 2137-2143, vol. 16(16).

Menten, P., et al., "The LD78☐ isoform of MIP-1a is the most potent CCR5 agonist and HIV-I-inhibiting chemokine," The Journal of Clinical Investigation, 1999, pp. R1-R5, vol. 104(4).

Noel, Daniele et al., "High In Vivo Production of a Model Monoclonal Antibody on Adenoviral Gene Transfer" Human Gene Therapy, 2002, pp. 1483-1493, vol. 13.

Øynebraten, I et al., "P19-39. Vaccibodies: a Novel Vaccine Strategy for HN that Target Viral Antigens to APC" Retrovilogy, Biomed Central Ltd., 2009.

Plückthun, Andreas and Pack, Peter, "New protein engineering approaches to multivalent and bispecific antibody fragments" Immunotechnology, 1997, pp. 83-105, vol. 3.

Proost Pet al., "Cleavage by CD26/dipeptidyl peptidase N converts the chemokine LD78beta into a Most Efficient Monocyte Attractant and CCR1 Agonist" Blood, 2000.

Rochlitz, Christoph F ., "Gene Therapy of Cancer" Swiss Medicine Weekly, 2001, pp. 4-9, vol. 131.

Ruffini, Pier Adelchi, et al., "Idiotypic vaccination for B-cell malignancies as a model for therapeutic cancer vaccines: from prototype protein to second generation vaccines" Haematologica, 2002, pp. 989-1001, vol. 87.

Ruffini, Pier Aldechi et al., "Human chemokine MIPlalpha increases efficiency of targeted DNA fusion vaccines" Vaccine, 2010, pp. 191-199,vol. 29.

Schall, T., et al., "Human Macrophage Inflammatory Protein a (MIP-1a) and MIP-1,B Chemokines Attract Distinct Population of Lymphocytes," J. Exp. Med., 1993, vol. 177, pp. 1821-1825.

Schiavo, R., et al., "Chemokine receptor targeting efficiently directs antigens to MHC class I pathways and elicits antigen-specific $CD8^+$ T-cell responses," Blood, 2006, vol. 107, pp. 4597-4605.

Schjetne, Karoline W. et al., "Delivery of Antigen to CD40 Induces Protective Immune Responses against Tumors" Journal of Immunology, 2007, pp. 4169-4176, vol. 178.

Schulenburg et al., "Amino Acid Sequence of the Light Chain from a Mouse Myeloma Protein with Anti-Hapten Activity: Evidence for a Third Type of Light Chain" PNAS, 1971, pp. 2623-2626, vol. 68, No. 11.

Simon, R. J., et al., "Peptoids: A modular approach to drug discovery," Proceedings of the National Academy of Sciences of the United States of America, 1992, pp. 9367-9371, vol. 89(20).

Slavin-Chiorini, Dale C. et al., "Biologic Properties of a CH2 Domain-Deleted Recombinant Immunoglobulin" Internal Journal of Cancer, 1993, pp. 97-103, vol. 53.

Snodgrass, H. R., et al., "Restricted a/☐ receptor gene usage of idiotype-specific major histocompatibility complex-restricted T cells: selection for CDR3-related sequences," *European Journal of Immunology*, 1992, pp. 2169-2172, vol. 22.

Stevenson et al., "DNA vaccines to attack cancer" PNAS, 2004, pp. 14646-14652 vol. 101.

Tang, DC., et al., "Genetic immunization is a simple method for eliciting an immune response," Nature, 1992, pp. 152-154, vol. 356(6365).

Tunheim, G., et al., "Human receptors of innate immunity (CD14, TLR2) are promising targets for novel recombinant immunoglobulin-based vaccine candidates," *Vaccine*, 2007, pp. 4723-4734, vol. 25(24).

Van Spriel, Annemiek B. et al., "Immunotherapeutic perspective for bispecific antibodies" Immunology Today, 2000, pp. 391-396, vol. 21, No. 8.

Verma, Inder M and Somia, Nikunj, "Gene Therapy—Promises, Problems, and Prospects" Nature, 1997, pp. 239-242, vol. 389.

Vile, RG et al., "Cancer Gene Therapy: Hard Lessons and New Courses" Gene Therapy, 2000, pp. 2-8, vol. 7, Macmilan Publishers Ltd.

Voskoglou-Nomikos, Theodora, "Clinical Predictive Value of the in Vitro Cell Line, Human Xenograft, and Mouse Allograft Preclinical Cancer Models" Clinical Cancer Research, 2003, pp. 4227-4239, vol. 9.

Wang, R., et al., Induction of the Antigen-Specific Cytotoxis T Lymphocytes in Humans by a Malaria DNA Vaccine, *Science*, 1998, 2003, pp. 476-480, vol. 282.

\* cited by examiner

A targeting unit:
1) hCCL3 isoforms
2) scFv from NIP-specific mAb dimerization unit:
h1+h4 exons and hγ3 CH3 antigenic unit:
1) scFv from MOPC315 mouse plasmacytoma
2) paired mouse Ck domains
3) influenza hemagglutinin

B

| | |
|---|---|
| LD78α | ASLAADTPTACC |
| LD78β | AP.................... |
| LD78β-2 | - - LA................ |
| LD78β(C11S) | APLAADTPTASC |

C

A

B

C

D

HOMODIMERIC PROTEIN CONSTRUCTS

CROSS-REFERENCE TO RELATED APPLICATIONS

This application is a divisional of U.S. application Ser. No. 13/805,709, filed Jan. 25, 2013, which is a national stage filing under 35 U.S.C. 371 of PCT/EP2011/060628 filed Jun. 24, 2011, which International Application was published by the International Bureau in English on Jun. 24, 2011, and application claims priority from U.S. Application No. 62/358,513, filed Jun. 25, 2010, which applications are hereby incorporated in their entirety by reference in this application.

FIELD OF THE INVENTION

The present invention relates to novel recombinant fusion proteins, such as human antibody-based molecules called Vaccibodies, which are able to trigger both a T cell- and B cell immune response. The present invention also relates to a method of treating a cancer or an infectious disease e.g. multiple myeloma or influenza by means of these specific fusion proteins.

BACKGROUND OF THE INVENTION

DNA vaccination is a technically simple way of inducing immune responses. However, success in small animals has not yet been reproduced in clinical trials. Several strategies are currently being pursued to increase efficacy of DNA vaccines.

Targeting of protein antigens to antigen-presenting cells (APC) can improve T- and B-cell responses. Recombinant immunoglobulin (Ig) molecules are well suited for this purpose. For example, short antigenic epitopes can replace loops between β-strands in the Ig constant domains while targeted antigen delivery is obtained by equipping the recombinant Ig with variable (V) regions specific for surface molecules on APC. However, such a strategy is unfit for larger antigens containing unidentified epitopes, moreover recombinant Ig molecules with short T cell epitopes fail to elicit antibodies against conformational epitopes. To overcome these limitations, targeted Ig-based homodimeric DNA vaccines (vaccibodies) have been generated that express infectious or tumor antigens with a size of at least 550 aa. with maintenance of conformational epitopes.

Chemokine (C—C motif) ligand 3 (CCL3) is a protein that in humans is encoded by the CCL3 gene. CCL3, also known as Macrophage inflammatory protein-1α (MIP-1α), is a cytokine belonging to the CC chemokine family that is involved in the acute inflammatory state in the recruitment and activation of polymorphonuclear leukocytes. While mouse CCL3 is a single copy gene encoding for a mature chemokine of 69 amino acids, the human homolog has been duplicated and mutated to generate two non-allelic variants, LD78α (CCL3) and LD78β (CCL3-L1), both showing a 74% homology with the mouse CCL3.

No DNA vaccine has so far been approved for human use due to lack of efficacy. Also there is no effective vaccine available for several infectious diseases. In particular, no therapeutic DNA cancer vaccine has been approved for human use.

WO 2004/076489 relates to recombinant human antibody-based molecule called Vaccibodies, which are able to trigger both a T cell- and B cell immune response.

US20070298051 relates to the use of MIP-1-alpha for enhancing the immune response to an immunogen in a mammal.

EP920522 relates to a polynucleotide vector vaccine comprising a cDNA target product that comprises a nucleotide sequence encoding a cytokine or chemokine.

Fredriksen A B et al. (Mol Ther 2006; 13:776-85) relates to DNA vaccines targeting tumor antigen to antigen-presenting cells.

Fredriksen A B and Bogen B (Blood 2007; 110: 1797-805) relates to mouse chemokine-idiotype fusion DNA vaccines.

OBJECT OF THE INVENTION

It is an object of embodiments of the invention to provide fusion proteins, which are able to trigger an efficient immune response for even weak antigens, such as idiotypic antigens derived from e.g. myeloma cells.

Furthermore it is an object of embodiments of the invention to provide polynucleotides, such as a DNA polynucleotide, encoding a fusion protein that trigger an efficient immune response against even weak antigens, such as idiotypic antigens derived from e.g. myeloma cells. These polynucleotides may be used as an immunostimulating composition or vaccine against a cancer or an infectious disease, characterized by a disease specific or disease associated antigen.

SUMMARY OF THE INVENTION

It has been found by the present inventor(s) that human chemokine LD78β, both full length and truncated versions thereof, are suited for use as targeting units that target antigenic epitopes to the surface of APC. The chemokine, or its truncated version are bound to chemokine receptors on the surface of APC in the form of a homodimeric protein construct, which facilitate that two identical chemokines are bound to provide more efficient targeting and signaling. The homodimeric construct further provide that two identical antigenic epitopes are delivered to the APC which in turn present them to T cells. Even with the relatively large size of the homodimeric protein constructs, cells are able to produce and export intact molecules.

So, in a first aspect, the present invention relates to a homodimeric protein of two identical amino acid chains, each amino acid chain comprising a targeting unit comprising an amino acid sequence having at least 80% sequence identity to the amino acid sequence 5-70 of SEQ ID NO:1, and an antigenic unit, the targeting unit and the antigenic unit being connected through a dimerization motif.

In a second aspect, the present invention relates to a homodimeric protein of two identical amino acid chains, each amino acid chain comprising a targeting unit comprising amino acids 3-70 of SEQ ID NO:1, and an antigenic unit, the targeting unit and the antigenic unit being connected through a dimerization motif.

In a third aspect, the present invention relates to a nucleic acid molecule encoding the monomeric protein which can form a homodimeric protein according to the invention.

In a further aspect, the present invention relates to a homodimeric protein according to the invention; for use as a medicament.

In a further aspect, the present invention relates to a nucleic acid molecule encoding the monomeric protein which can form a homodimeric protein according to the invention; for use as a medicament.

In a further aspect, the present invention relates to a pharmaceutical composition comprising a homodimeric protein according to the invention.

In a further aspect, the present invention relates to a pharmaceutical composition comprising a nucleic acid molecule encoding the monomeric protein which can form a homodimeric protein according to the invention.

In a further aspect, the present invention relates to a host cell comprising a nucleic acid molecule encoding the monomeric protein which can form a homodimeric protein according to the invention.

In a further aspect, the present invention relates to a method for preparing a homodimeric protein according to the invention, the method comprising
 a) transfecting the nucleic acid molecule according to the invention into a cell population;
 b) culturing the cell population;
 c) collecting and purifying the homodimeric protein expressed from the cell population.

In a further aspect the present invention relates to a vaccine against a cancer or an infectious disease comprising an immunologically effective amount of a homodimeric protein according to the invention or nucleic acid molecule encoding the monomeric protein which can form the homodimeric protein according to the invention, wherein said vaccine is able to trigger both a T-cell- and B-cell immune response and wherein said homodimeric protein contain an antigenic unit related to said cancer or infectious disease.

In a further aspect the present invention relates to an immunomodulating or immunostimulating composition against a cancer or an infectious disease comprising an immunologically effective amount of a homodimeric protein according to the invention or nucleic acid molecule encoding the monomeric protein which can form the homodimeric protein according to the invention, wherein said immunomodulating or immunostimulating composition is able to trigger both a T-cell- and B-cell immune response and wherein said homodimeric protein contain an antigenic unit related to said cancer or infectious disease.

In a further aspect the present invention relates to a method of treating a cancer or an infectious disease in a patient, the method comprising administering to the patient in need thereof, a homodimeric protein according to the invention, or the nucleic acid molecule encoding the monomeric protein which can form the homodimeric protein according to the invention, wherein said homodimeric protein contain an antigenic unit related to said cancer or infectious disease.

LEGENDS TO THE FIGURE

FIG. 1. Fusion vaccines used in this study. (A) Schematic structure of a homodimeric chemokine-antigen fusion protein (vaccibody). Targeting, dimerization and antigenic units are indicated as are moieties expressed in the various units. In all constructs, the dimerization unit and hinge are derived from human IgG3. A $G_3S_2G_3SG$ linker connects hinge exons h1+h4 to the CH3 domain. A GLSGL linker connects CH3 and the antigenic unit, whereas a $(G_4S)_3$ linker connects $V_H$ and $V_L$ in the antigenic unit. (B) NH2 terminal sequences (aa. 1-12) of human CCL3 isoforms, and their point mutated control (C11S, indicated in bold). Slash indicates deletion. (C) The C11S point mutation putatively destroys a S—S bridge in the chemokine structure (right).

Figure 2:
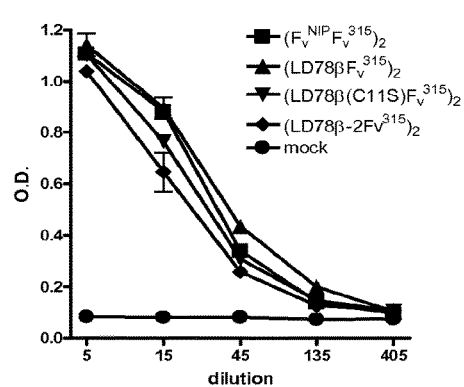
Figure 2:
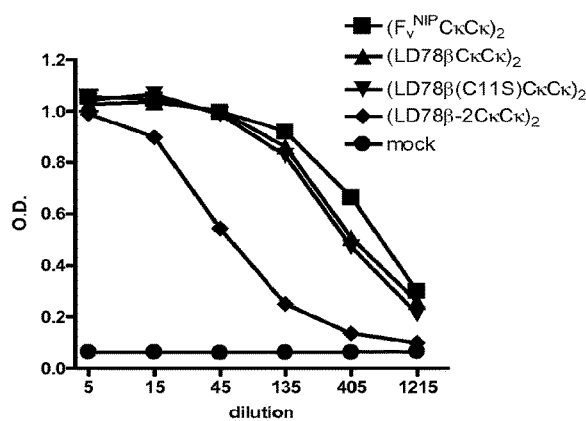
Figure 2:
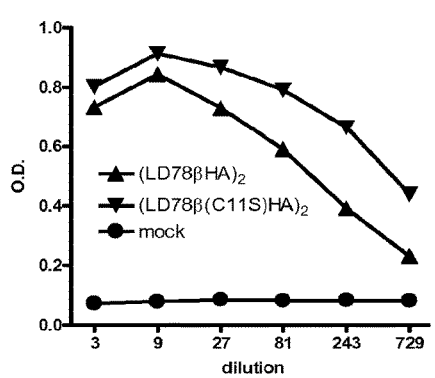
Figure 2:
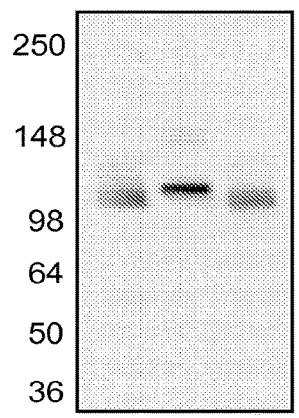

FIG. 2. Characterization of LD78β-expressing vaccibodies by ELISA and Western blot. Supernatants of transiently transfected 293E cells collected at day 5 were tested in ELISA by using mAbs specific for different components of the vaccibody molecules. (A), $scFv^{315}$ encoding vaccibodies with indicated targeting units were evaluated by binding to DNP-BSA coat (binds $scFv^{315}$) and detection with biotinylated HP6017 (binds CH3 dimerization motif). (B), CκCκ-encoding vaccibodies, with indicated targeting units, were evaluated by binding to 187.1 mAb (binds mouse Cκ) coat and detection with biotinylated 187.1 mAb, (C), HA-encoding vaccibodies, with indicated targeting units, were evaluated by binding to MCA878-G (anti-CH3 dimerization motif) and detection with biotinylated anti-HA mAb H36-4-52 (D), Western blot of vaccibodies probed with biotinylated HP6017 under non-reducing conditions. Left to right, $(LD78\beta Fv^{315})2$, $(LD78\beta C11SFv^{315})2$ and $(LD78\beta\text{-}2Fv^{315})2$.

Figure 3:
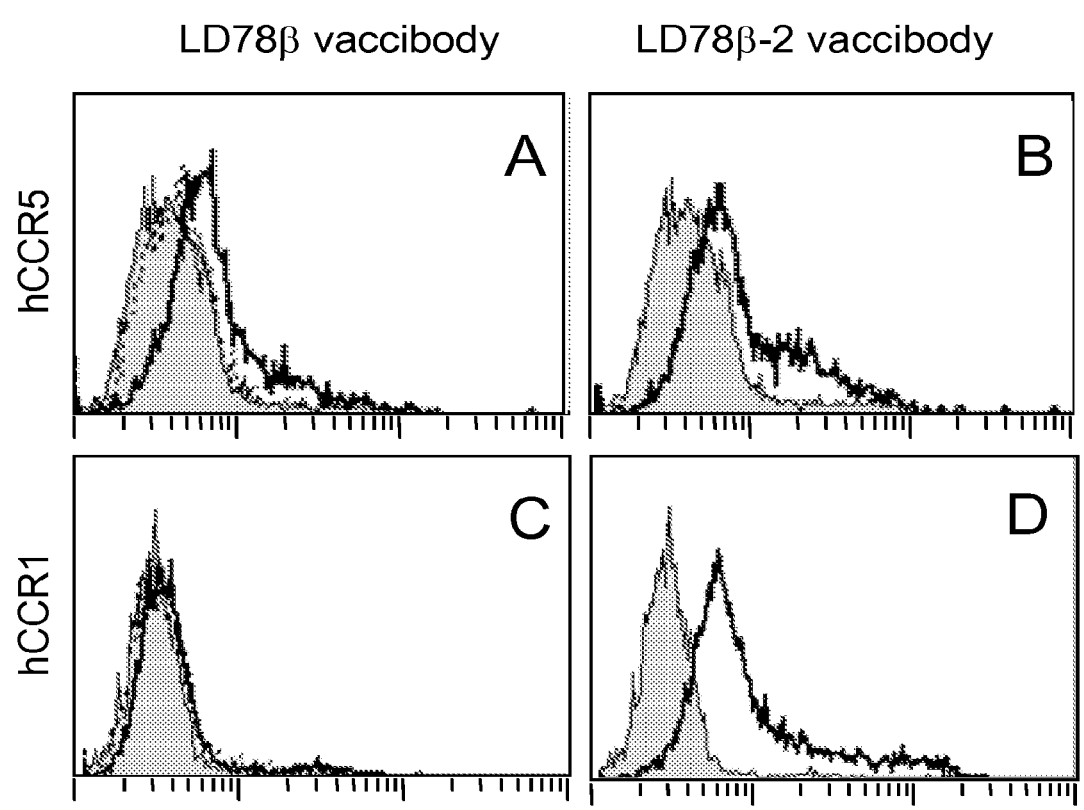

FIG. 3. LD78β vaccibody proteins bind chemokine receptors on human cells. The indicated homodimeric vaccibody proteins at 25 μg/mL were admixed with HEK 293 cells stably transfected with either human CCR5 (A, B), or human CCR1 (C, D). Bound vaccibody proteins were detected by biotinylated Ab2.1-4 mAb specific for the $scFv^{315}$ antigenic unit, followed by PE-streptavidin. Bold lines: $(LD78\beta Fv^{315})2$ (A, C) and $(LD78\beta\text{-}2Fv^{315})2$ (B, D) vaccibodies. Dashed line in (A): $(LD78\beta(C11S)Fv^{315})2$. Shaded histogram: biotinylated Ab2.1-4 mAb and PE-streptavidin alone.

Figure 4:
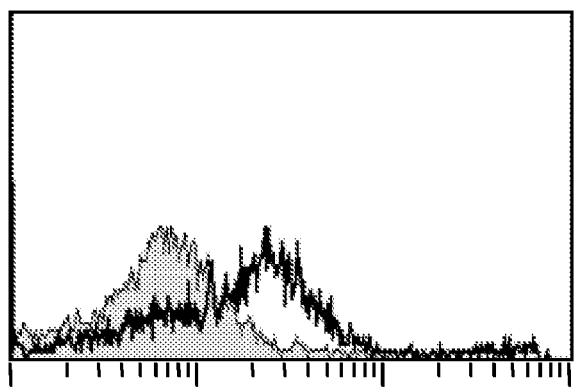
Figure 4:
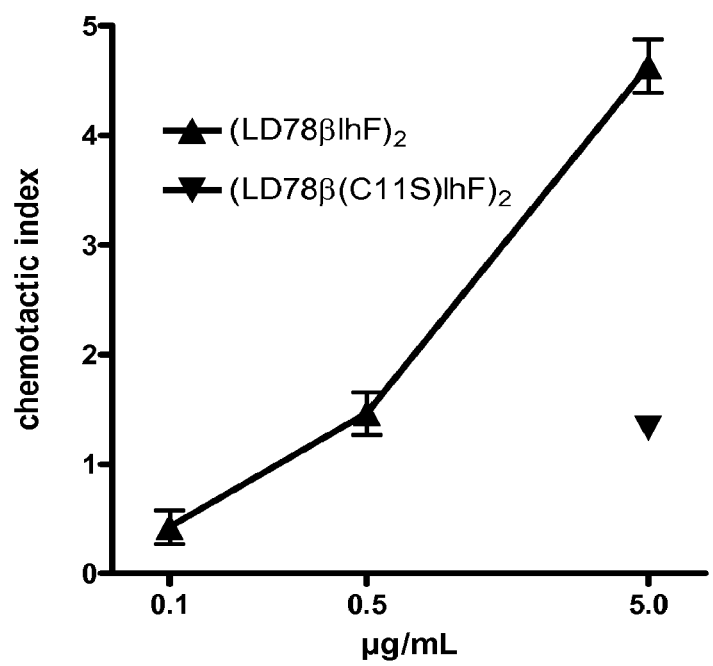

FIG. 4. LD78β vaccibody proteins bind mouse chemokine receptors and induce chemotaxis of murine cells. $(LD78\beta Fv^{315})2$ vaccibody (open histogram), but not the C11S variant (shaded histogram), binds to CD11b+ BALB/c splenocytes (A) and displays chemotactic activity on lymphocytic Esb/MP cells (B).

Figure 5:
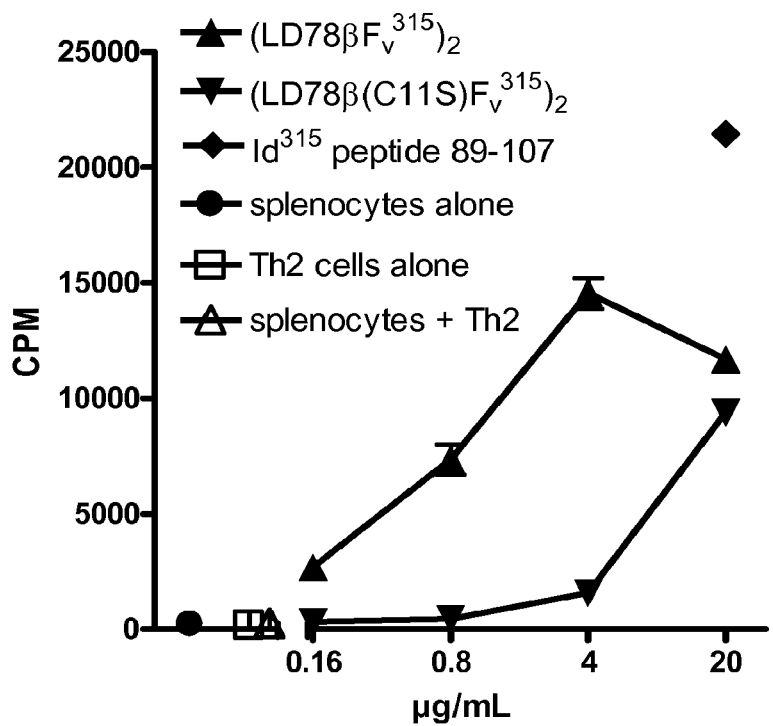
Figure 5:
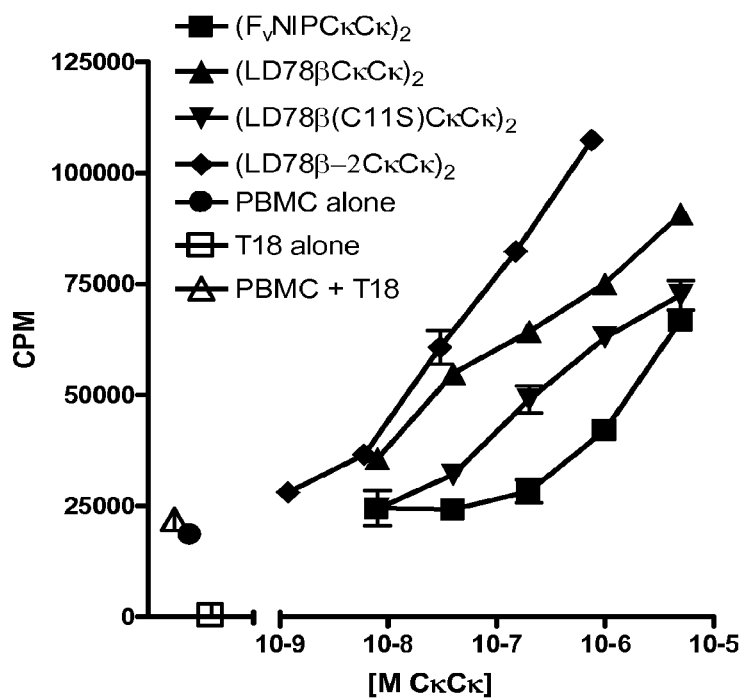

FIG. 5. Vaccibody with LD78β targeting unit efficiently delivers antigen to mouse (A) and human (B) APC for MHC class II-restricted presentation to CD4+ T cells. (A) Different amounts of purified vaccibodies having $scFv^{315}$ as antigenic unit were admixed with irradiated (8 gy) BALB/c splenocytes, followed by addition of Id($\lambda 2^{315}$)-specific Th2 T cells from TCR transgenic mice. After 48 hrs cultures were pulsed with 3H thymidine for 24 hrs. (B) Different amounts of mouse Cκ-containing vaccibody supernatants (expressed as molar concentration (M) of CκCκ) from transiently transfected 293E cells were admixed with DR4*01 PBMCs which were then irradiated and admixed with mouse Cκ-specific T18 T cells. After 48 hrs the plate was pulsed with 3H thymidine for 24 hrs.

Figure 6:
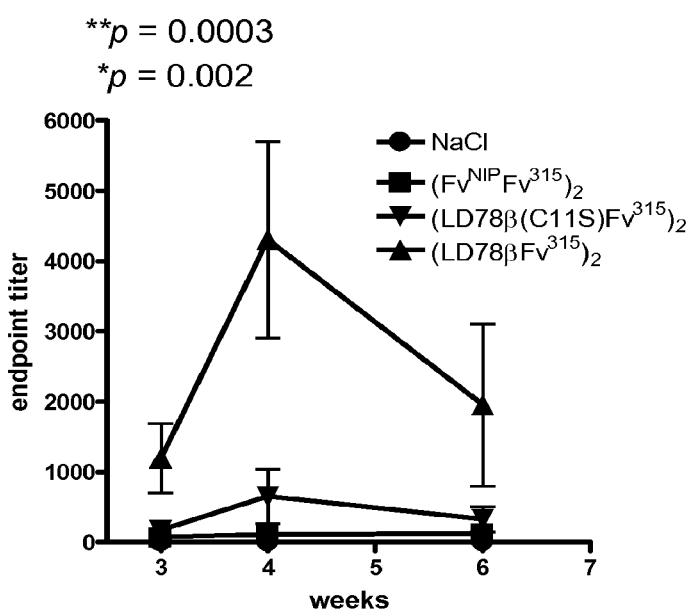
Figure 6:
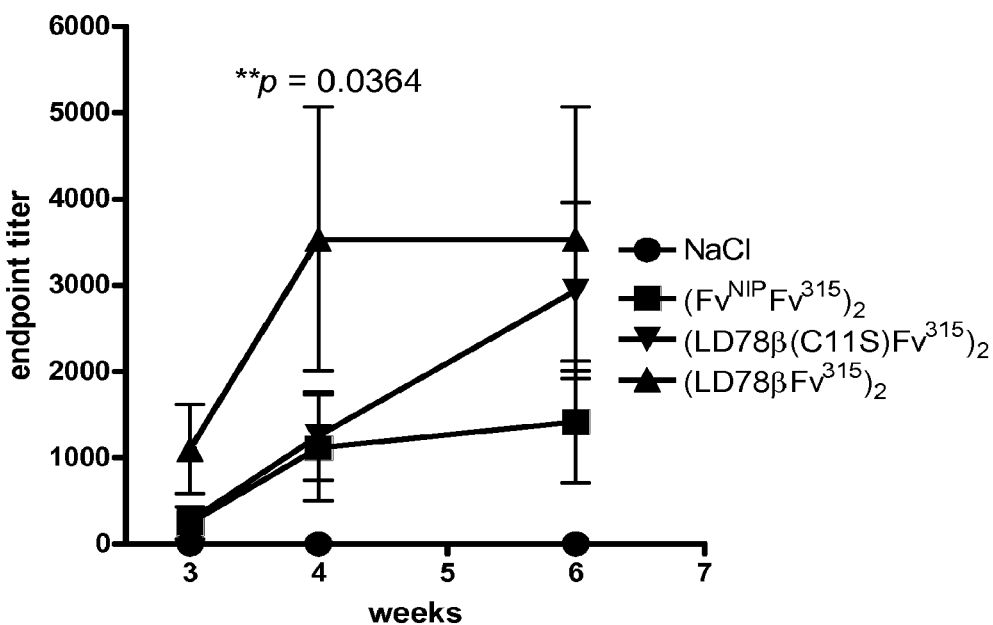

FIG. 6. Anti-$Id^{315}$ immune responses in mice immunized with LD78 μ$Fv^{315}$ vaccibody DNA. Mice were immunized by intradermal administration of DNA immediately followed by electroporation of the injection site. Type of vaccibodies and controls are indicated. Sera obtained 3 weeks later were tested for anti-Id IgG1 (A) or IgG2a (B) antibodies binding the M315 myeloma protein. Mean of up to 7 mice per group is shown. p values refer to LD78β vs LD78β (C11S) (*), and to LD78β vs (FvNIP)2 vaccibody (**) at week 4.

Figure 7:
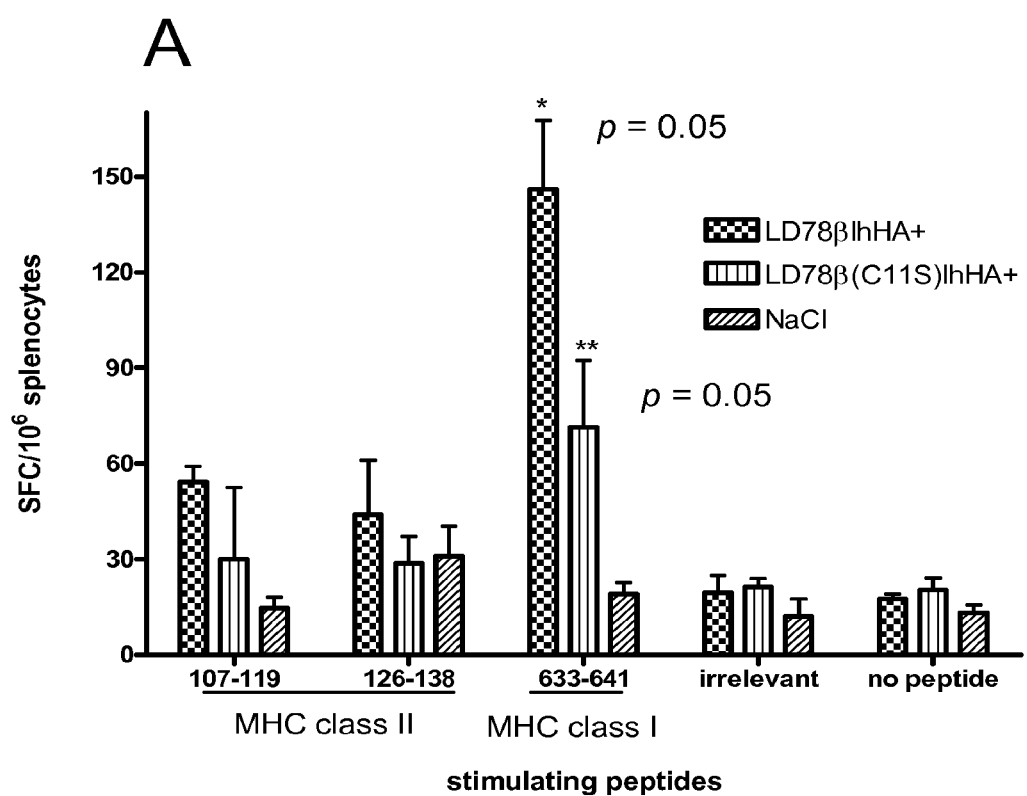

FIG. 7. Induction of CD4+ and CD8+ influenza hemagglutinin-specific T cell responses by LD78β-vaccibodies. Mice (n=3) were immunized by intradermal administration of DNA immediately followed by electroporation of the injection site (Dermavax, Cytopulse, USA). Type of vaccibodies and controls are indicated. Mice were sacrificed 3 weeks later and individual splenocyte suspensions used in ELISPOT assays with the indicated MHC class II- and class I-restricted synthetic HA peptides, or irrelevant peptide. $IFN_\gamma$ responses were evaluated. p values refer to LD78β vs LD78βC11S and LD78β vs 0.9% NaCl (*), and to LD78βC11S vs 0.9% NaCl (**).

Figure 8:
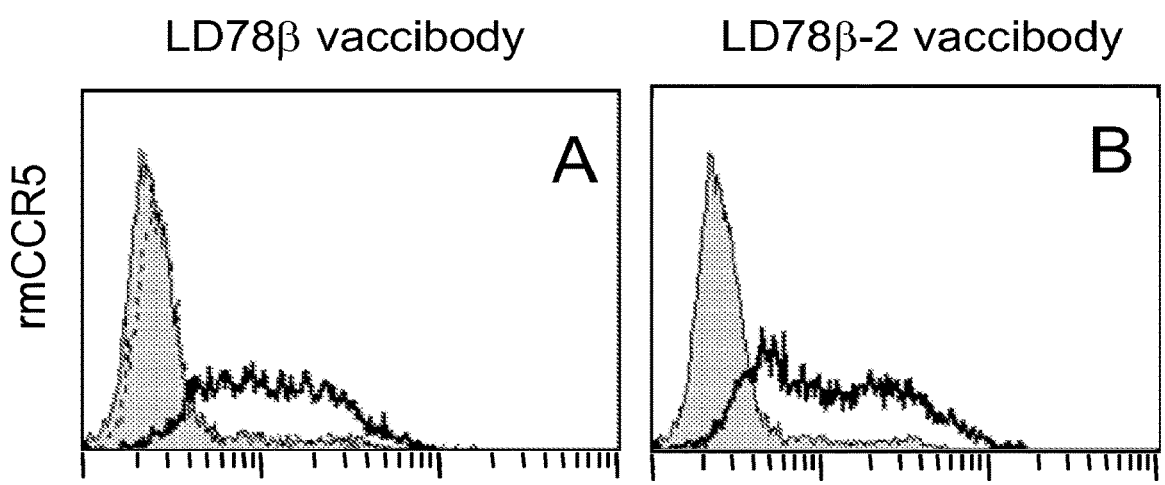

FIG. 8. LD78β vaccibodies binds to rhesus macaque CCR5. Vaccibody proteins at 25 μg/mL were admixed with HEK 293 stably transfected with Rhesus macaque CCR5. Bound vaccibody proteins were detected by biotinylated Ab2.1-4 mAb specific for the scFv$^{315}$ antigenic unit followed by PE-streptavidin. Bold line indicates vaccibodies (LD78βFv$^{315}$)2 in (A) and (LD78β-2Fv$^{315}$)2 in (B). Dashed line in (A) indicates (LD78β(C11S)Fv$^{315}$)2 vaccibody. In both A and B shaded histograms indicate biotinylated Ab2.1-4 mAb and PE-streptavidin alone.

Figure 9:
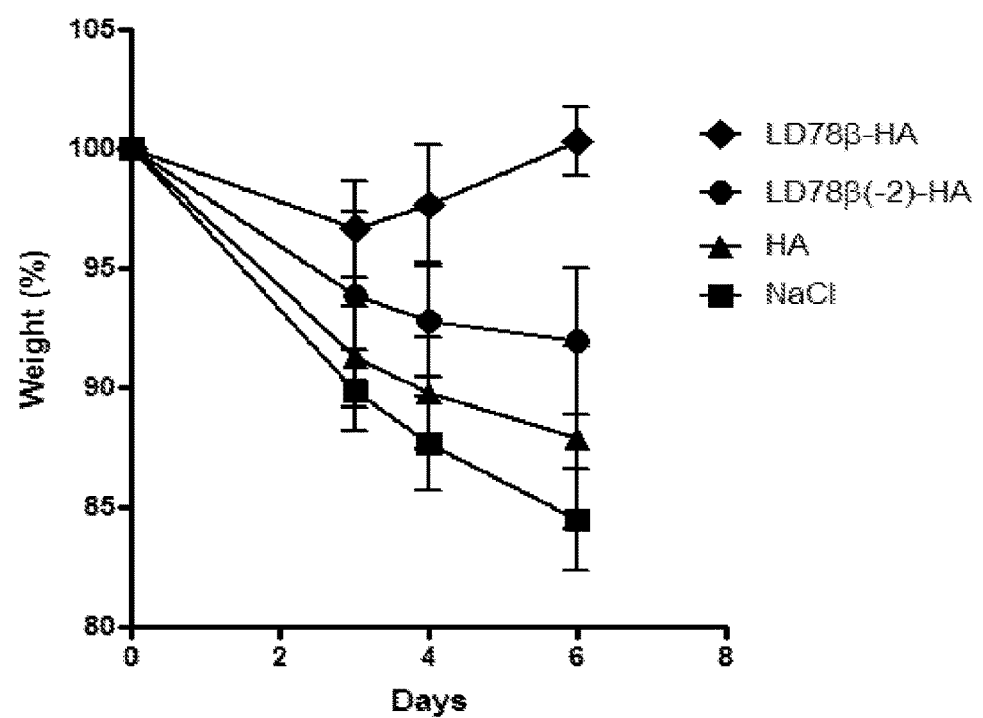

FIG. 9. Protection against a lethal challenge with influenza. Balb/c mice were immunized once intradermally with 25 μg DNA in combination with electroporation (DermaVax), and challenged after 14 days (n=6/group) with a lethal dose of PR8 influenza virus (H1N1).

DETAILED DISCLOSURE OF THE INVENTION

Efficacy of DNA vaccines needs to be increased. A promising strategy in mice is to construct DNA encoding a fusion protein that target antigen to antigen-presenting cells (APC) via chemokine receptors. It is crucial to extend this strategy for improved DNA vaccines to large animals and humans. According to the present invention, human MIP-1α chemokines may be fused with different antigenic units. The fusion proteins retain functional activity and conformational correctness of targeting and antigenic units, respectively. Fusion proteins may improve responses of cloned human CD4+ T cells. Moreover, since LD78β fusion proteins binds mouse chemokine receptors, human DNA vaccines can be tested in mice. LD78β DNA fusion vaccines according to the present invention induced improved T cell and antibody responses in mice following plasmid injection and skin electroporation. CD8+ T cell responses are particularly enhanced, indicating efficient cross-priming. A two amino acid NH$_2$-truncated version of LD78β is by the present inventors proved to have superior binding to mouse cells compared to the full length LD78β in vitro. Surprisingly the full length version of LD78 β have showed superior effect in an in vivo mouse model. LD78β-vaccine proteins was found by the inventors of the present invention to bind Rhesus macaque CCR5, setting the stage for targeted DNA immunization in non human primates.

Vaccibodies according to the present invention may be recombinant Ig-based homodimeric vaccines, each chain being composed of a targeting unit directly attached to Ig hinge and CH3, the combination of which induces covalent homodimerization (FIG. 1A).

While mouse CCL3 is a single copy gene encoding for a mature chemokine of 69 aa., the human homolog has been duplicated and mutated to generate two non-allelic variants, LD78α (CCL3) and LD78β (CCL3-L1), both showing a 74% homology with the mouse CCL3. The two variants share a 96% homology, the differences being S or P at position 2 and a swap between G and S at positions 39 and 47.

According to the present invention, human CCL3 variants and different antigenic units, may be constructed and expressed as functional proteins. In particular, the present invention relates to the utilization of LD78β and its natural isoforms in fusion vaccines to target antigen delivery to antigen-presenting cells.

The vaccibodies according to the present invention aims at improving the immunogenicity of vaccines (immunostimulating compositions). Included within the present invention are DNA vaccines encoding a fusion protein that targets antigen delivery to LD78β receptors on professional antigen-presenting cells.

Vaccibodies equipped with LD78β or NH$_2$-truncated versions hereof were by the inventors of the present invention found to bind cells expressing murine or Rhesus macaque or human CCR1 and/or CCR5 (receptors for LD78β) in vitro and afforded augmented antigen delivery in vitro as well as increased humoral and cellular immune responses in vivo following DNA injection and electroporation, as compared with control, non-targeted vaccibodies.

The recombinant proteins according to the present invention may be human antibody-like molecules useful in the treatment of many types of cancer or infectious diseases, including multiple myeloma. These molecules, also referred to as Vaccibodies, bind APC and are able to trigger both T cell and B cell immune response. Moreover, Vaccibodies bind divalently to APC to promote a more efficient induction of a strong immune response. Vaccibodies comprise a dimer of a monomeric unit that consists of a targeting unit with specificity for a surface molecule on APC, connected through a dimerization motif, such as a hinge region and a Cγ3 domain, to an antigenic unit, the later being in the COOH-terminal or NH$_2$-terminal end. The present invention also relates to a DNA sequence coding for this recombinant protein, to expression vectors comprising these DNA sequences, cell lines comprising said expression vectors, to treatment of mammals preferentially by immunization by means of Vaccibody DNA, Vaccibody RNA, or Vaccibody protein, and finally to pharmaceuticals and a kit comprising the said molecules.

The dimerization motif in the proteins according to the present invention may be constructed to include a hinge region and an immunoglobulin domain (e.g. Cγ3 domain), e.g. carboxyterminal C domain ($C_H3$ domain), or a sequence that is substantially homologous to said C domain. The hinge region may be Ig derived and contributes to the dimerization through the formation of an interchain covalent bond(s), e.g. disulfide bridge(s). In addition, it functions as a flexible spacer between the domains allowing the two targeting units to bind simultaneously to two target molecules on APC expressed with variable distances. The immunoglobulin domains contribute to homodimerization through noncovalent interactions, e.g. hydrophobic interactions. In a preferred embodiment the $C_H3$ domain is derived from IgG. These dimerization motifs may be exchanged with other multimerization moieties (e.g. from other Ig isotypes/subclasses). Preferably the dimerization motif is derived from native human proteins, such as human IgG.

It is to be understood that the dimerization motif may have any orientation with respect to antigenic unit and targeting unit. In one embodiment the antigenic unit is in the COOH-terminal end of the dimerization motif with the targeting unit in the N-terminal end of the dimerization motif. In another embodiment the antigenic unit is in the N-terminal end of the dimerization motif with the targeting unit in the COOH-terminal end of the dimerization motif.

International application WO 2004/076489, which is hereby incorporated by reference discloses nucleic acid sequences and vectors, which may be used according to the present invention.

The proteins according to the present invention may be suitable for induction of an immune response against any polypeptide of any origin. Any antigenic sequence of sufficient length that include a specific epitope may be used as the antigenic unit in the proteins according to the invention. The minimal length of such antigenic unit may be around 9 amino acids. Accordingly in some embodiments, the antigenic unit comprises an amino acid sequence of at least 9 amino acids corresponding to at least about 27 nucleotides in a nucleic acids sequence encoding such antigenic unit. Such an antigenic sequence may be derived from cancer proteins or infectious agents. Examples of such cancer sequences are telomerase, more specifically hTERT, tyrosinase, TRP-1/TRP-2 melanoma antigen, prostate specific antigen and idiotypes. The infectious agents can be of bacterial, e.g. tuberculosis antigens and OMP31 from brucellosis, or viral origin, more specifically HIV derived sequences like e.g. gp120 derived sequences, glycoprotein D from HSV-2, and influenza virus antigens like hemagglutinin, nuceloprotein and M2. Insertion of such sequences in a Vaccibody format might also lead to activation of both arms of the immune response. Alternatively the antigenic unit may be antibodies or fragments thereof, such as the C-terminal scFv derived from the monoclonal Ig produced by myeloma or lymphoma cells, also called the myeloma/lymphoma M component in patients with B cell lymphoma or multiple myeloma. Such scFv represents idiotypic antigen.

In one particular embodiment, also used in the examples described herein, the antigenic unit of the protein according to the present invention is the scFv of the myeloma protein M315 derived from the BALB/c plasmacytoma MOPC315.4. The $\lambda 2^{315}$ light chain of M315 harbors three defined somatic mutations in the CDR3 loop and functions as a model idiotypic T cell epitope in a well defined system (Bogen, Malissen et al. 1986; Bogen and Lambris 1989).

Immunization by means of Vaccibody protein, Vaccibody DNA, or Vaccibody RNA, the latter two executed e.g. by intramuscular or intradermal injection with or without a following electroporation, are all feasible methods.

The targeting unit of the proteins according to the invention targets the protein to APC through binding to chemokine receptors.

The proteins according to the present invention may be genetically assembled, and the DNA transfected into a suitable host cell, such as NS0 cells, 293E cells, CHO cells or COS-7 cells. Transfectants produce and secrete the recombinant proteins.

The present invention relates to a pharmaceutical comprising the above described recombinant based proteins, DNA/RNA sequences, or expression vectors according to the invention. Where appropriate, this pharmaceutical additionally comprises a pharmaceutically compatible carrier. Suitable carriers and the formulation of such pharmaceuticals are known to a person skilled in the art. Suitable carriers are e.g phosphate-buffered common salt solutions, water, emulsions, e.g. oil/water emulsions, wetting agents, sterile solutions etc. The pharmaceuticals may be administered orally or parenterally. The methods of parenteral administration comprise the topical, intra-arterial, intramuscular, subcutaneous, intramedullary, intrathekal, intraventricular, intravenous, intraperitoneal or intranasal administration. The suitable dose is determined by the attending physician and depends on different factors, e.g. the patient's age, sex and weight, the kind of administration etc. Furthermore, the present invention relates to a vaccine composition or immunostimulating compositions against cancer or infectious diseases comprising an immunologically effective amount of the nucleic acid encoding the molecule of the invention or degenerate variants thereof, wherein said composition is able to trigger both a T-cell- and B-cell immune response.

The present invention also relates to a kit comprising Vaccibody DNA, RNA, or protein for diagnostic, medical or scientific purposes.

The invention further relates to a method of preparing the recombinant molecule of the invention comprising, transfecting the vector comprising the molecule of the invention into a cell population; culturing the cell population; collecting recombinant protein expressed from the cell population; and purifying the expressed protein.

The above described nucleotide sequences may preferably be inserted into a vector suited for gene therapy, e.g. under the control of a specific promoter, and introduced into the cells. In a preferred embodiment the vector comprising said DNA sequence is a virus, e.g an adenovirus, vaccinia virus or an adeno-associated virus. Retroviruses are particularly preferred. Examples of suitable retroviruses are e.g. MoMuLV or HaMuSV. For the purpose of gene therapy, the DNA/RNA sequences according to the invention can also be transported to the target cells in the form of colloidal dispersions. They comprise e.g. liposomes or lipoplexes.

The present invention also encompasses the use of polypeptides or domains or motifs within the polypeptides having a degree of sequence identity or sequence homology with amino acid sequence(s) defined herein or with a polypeptide having the specific properties defined herein. The present invention encompasses, in particular, peptides having a degree of sequence identity with SEQ ID NO: 1, or homologues thereof. Here, the term "homologue" means an entity having sequence identity with the subject amino acid sequences or the subject nucleotide sequences, where the subject amino acid sequence preferably is SEQ ID NO: 1.

In one aspect, the homologous amino acid sequence and/or nucleotide sequence should provide and/or encode a polypeptide which retains the functional activity and/or enhances the activity of a polypeptide of SEQ ID NO: 1.

In the present context, a homologous sequence is taken to include an amino acid sequence which may be at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:
  i) assignment of a penalty score each time a gap is inserted (gap penalty score),
  ii) assignment of a penalty score each time an existing gap is extended with an extra position (extension penalty score),
  iii) assignment of high scores upon alignment of identical amino acids, and
  iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| Substitution matrix: | Gonnet 250 |
|---|---|
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:
Gap opening penalty: 10
Gap extension penalty: 0.05
Gap separation penalty range: 8
Score matrix: blosum62mt2

Thus, the present invention also encompasses the use of variants, homologues and derivatives of any amino acid sequence of a protein, polypeptide, motif or domain as defined herein, particularly those of SEQ ID NO: 1.

The sequences, particularly those of variants, homologues and derivatives of SEQ ID NO: 1, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriyl-alanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-conservative substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al. (1992), Horwell DC. (1995).

In one embodiment, the variant targeting unit used in the homodimeric protein according to the present invention is variant having the sequence of amino acids 5-70 of SEQ ID NO:1 and having at least at least 65%, at least 70%, at least 75%, at least 78%, at least 80%, at least 85%, at least 90%, at least 95%, at least 96%, at least 97%, at least 98% or at least 99% amino acid sequence identity therewith.

In one aspect, preferably the protein or sequence used in the present invention is in a purified form. The term "purified" means that a given component is present at a high level. The component is desirably the predominant active component present in a composition.

A "variant" or "variants" refers to proteins, polypeptides, units, motifs, domains or nucleic acids. The term "variant" may be used interchangeably with the term "mutant." Variants include insertions, substitutions, transversions, truncations, and/or inversions at one or more locations in the amino acid or nucleotide sequence, respectively. The phrases "variant polypeptide", "polypeptide", "variant" and "variant enzyme" mean a polypeptide/protein that has an amino acid sequence that has been modified from the amino acid sequence of SEQ ID NO: 1. The variant polypeptides include a polypeptide having a certain percent, e.g., 80%, 85%, 90%, 91%, 92%, 93%, 94%, 95%, 96%, 97%, 98%, or 99%, of sequence identity with SEQ ID NO: 1, or the amino acid sequence 5-70 of SEQ ID NO: 1.

"Variant nucleic acids" can include sequences that are complementary to sequences that are capable of hybridizing to the nucleotide sequences presented herein. For example, a variant sequence is complementary to sequences capable of hybridizing under stringent conditions, e.g., 50° C. and 0.2×SSC (1×SSC=0.15 M NaCl, 0.015 M sodium citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein. The melting point (Tm) of a variant nucleic acid may be about 1, 2, or 3° C. lower than the Tm of the wild-type nucleic acid. The variant nucleic acids include a polynucleotide having a certain percent, e.g., 80%, 85%, 90%, 95%, or 99%, of sequence identity with the nucleic acid encoding SEQ ID NO: 1 or encoding the monomeric protein which can form the homodimeric protein according to invention.

The term "homodimeric protein" as used herein refers to a protein comprising two individual identical strands of amino acids, or subunits held together as a single, dimeric protein by either hydrogen bonding, ionic (charged) interactions, actual covalent disulfide bonding, or some combination of these interactions.

The term "dimerization motif", as used herein, refers to the sequence of amino acids between the antigenic unit and the targeting unit comprising the hinge region and the optional second domain that may contribute to the dimerization. This second domain may be an immunoglobulin domain, and optionally the hinge region and the second domain are connected through a linker. Accordingly the dimerization motif serve to connect the antigenic unit and the targeting unit, but also contain the hinge region that facilitates the dimerization of the two monomeric proteins into a homodimeric protein according to the invention.

The term "targeting unit" as used herein refers to a unit that delivers the protein with its antigen to mouse or human APC for MHC class II-restricted presentation to CD4+ T cells or for providing cross presentation to CD8+ T cells by MHC class I restriction.

The term "antigenic unit" as used herein refers to any molecule, such as a peptide which is able to be specifically recognized by an antibody or other component of the immune system, such as a surface receptor on T-cells. Included within this definition are also immunogens that are able to induce an immune response, such as idiotype immunogens of antibodies. The terms "epitope" or "antigenic epitope" is used to refer to a distinct molecular surface, such as a molecular surface provided by a short peptide sequence within an antigenic unit. In some embodiments the antigenic unit comprises two ore more antigenic epitopes.

The term "hinge region" refers to a peptide sequence of the homodimeric protein that facilitates the dimerization, such as through the formation of an interchain covalent bond(s), e.g. disulfide bridge(s). The hinge region may be Ig derived, such as hinge exons h1+h4 of an Ig, such as IgG3.

The term "immunostimulating composition" as used herein refers to any therapeutic composition that is capable to activate the immune system, e.g., by activating or inhibiting lymphocyte functions, in particular T-cell functions like T-cell activation.

Specific Embodiments of the Invention

In some embodiments the antigenic unit is a cancer associated or a cancer specific antigen.

The term "cancer associated antigen" refers to any antigen, which in not necessarily specific for a certain cancer, but overexpressed on the surface of the cancer cells of this cancer. The term may be used interchangeably with the term "cancer antigens".

In some embodiments the antigenic unit is an antigenic scFv. In some embodiments a linker, such as a $(G_4S)_3$ linker, connects the $V_H$ and $V_L$ in the antigenic scFv. In some embodiments the antigenic scFv is derived from a monoclonal Ig produced by myeloma or lymphoma cells.

In some embodiments the antigenic unit is a telomerase, or a functional part thereof. In some embodiments the telomerase is hTERT.

In some embodiments the antigenic unit is a melanoma antigen. In some embodiments the melanoma antigen is tyrosinase, TRP-1, or TRP-2.

In some embodiments the antigenic unit is a prostate cancer antigen. In some embodiments the prostate cancer antigen is PSA.

In some embodiments the antigenic unit is a cervix cancer antigen. In some embodiments the cervix cancer antigen is selected from the list consisting of human papilloma virus E1, E2, E4, E6, and E7.

In some embodiments the antigenic unit is derived from a bacterium.

In some embodiments the bacterium derived antigenic unit is a tuberculosis antigen.

In some embodiments the bacterium derived antigenic unit is a brucellosis antigen.

In some embodiments the antigenic unit is derived from a virus.

In some embodiments the virus derived antigenic unit is derived from HIV. In some embodiments the HIV derived antigenic unit is derived from gp120 or Gag.

In some embodiments the antigenic unit is selected from the list consisting of influenza virus hemagglutinin (HA), nucleoprotein, and M2 antigen; Herpes simplex 2 antigen glycoprotein D; and a Human Papilloma virus antigen, such as any one selected from the list consisting of E1, E2, E6, E7, L1 and L2.

In some embodiments the dimerization motif comprises a hinge region and optionally another domain that facilitate dimerization, such as an immunoglobulin domain, optionally connected through a linker.

In some embodiments the hinge region is Ig derived, such as derived from IgG3.

In some embodiments the hinge region has the ability to form one, two, or several covalent bonds. In some embodiments the covalent bond is a disulphide bridge.

In some embodiments the immunoglobulin domain of the dimerization motif is a carboxyterminal C domain, or a sequence that is substantially homologous to said C domain. In some embodiments the carboxyterminal C domain is derived from IgG.

In some embodiments the immunoglobulin domain of the dimerization motif has the ability to homodimerize.

In some embodiments the immunoglobulin domain of the dimerization motif has the ability to homodimerize via noncovalent interactions. In some embodiments the noncovalent interactions are hydrophobic interactions.

In some embodiments the dimerization domain does not comprise the CH2 domain.

In some embodiments the dimerization motif consist of hinge exons h1 and h4 connected through a linker to a $C_H3$ domain of human IgG3.

In some embodiments the linker that connect the hinge region and another domain that facilitate dimerization, such as an immunoglobulin domain, is a $G_3S_2G_3SG$ linker.

In some embodiments the antigenic unit and the dimerization motif is connected through a linker, such as a GLSGL linker.

In some embodiments the targeting unit comprises amino acids 3-70 of SEQ ID NO:1.

In some embodiments the targeting unit consists of amino acids 5-70 of SEQ ID NO:1.

In some embodiments the targeting unit consists of amino acids 3-70 of SEQ ID NO:1.

In some embodiments the targeting unit consists of amino acids 1-70 of SEQ ID NO:1.

In some embodiments the homodimeric protein do not comprise amino acids 1-70 of SEQ ID NO:1.

In some embodiments the targeting unit comprises amino acids 3-70 of SEQ ID NO:2.

In some embodiments the targeting unit consists of amino acids 5-70 of SEQ ID NO:2.

In some embodiments the targeting unit consists of amino acids 3-70 of SEQ ID NO:2.

In some embodiments the targeting unit consists of amino acids 1-70 of SEQ ID NO:2.

In some embodiments the homodimeric protein do not comprise amino acids 1-70 of SEQ ID NO:2.

In some embodiments the targeting unit consists of not more than 68 amino acids, such as 68, 67, or 66 amino acids.

In some embodiments the targeting unit do not contain the amino acid sequence AP at positions 1 and 2 of the targeting unit.

In some embodiments the homodimeric protein is a first homodimeric protein having increased affinity as compared to the affinity of a second homodimeric protein, which second homodimeric protein only differs from said first homodimeric protein by having a targeting unit, which consists of amino acids 1-70 of SEQ ID NO:2; the increased affinity being for any one chemokine receptor selected from CCR1, CCR3 and CCR5. In some embodiments the nucleic acid molecule according to invention is comprised by a vector.

In some embodiments the nucleic acid molecule according to the invention is formulated for administration to a patient to induce production of the homodimeric protein in said patient.

In some embodiments the vaccine or immunostimulating composition according to the invention comprises a pharmaceutically acceptable carrier and/or adjuvant.

In some embodiments the cancer treated by a vaccine or immunostimulating composition or pharmaceutical compositions according to the present invention is multiple myeloma or lymphoma, malignant melanoma, HPV induced cancers, prostate cancer, breast cancer, lung cancer, ovarian cancer, and/or liver cancer.

In some embodiments the infectious disease treated by a vaccine or immunostimulating composition or pharmaceutical compositions according to the present invention is selected from the list consisting of influenza, Herpes, CMV, HPV, HBV, brucellosis, HIV, HSV-2 and tuberculosis.

Numbered Embodiments of the Invention

1. A homodimeric protein of two identical amino acid chains, each amino acid chain comprising a targeting unit comprising an amino acid sequence having at least 80% sequence identity to the amino acid sequence 5-70 of SEQ ID NO:1, and an antigenic unit, the targeting unit and the antigenic unit being connected through a dimerization motif.

2. The homodimeric protein according to embodiment 1, wherein the antigenic unit is an antigenic scFv.

3. The homodimeric protein according to embodiments 1 or 2, wherein a linker, such as a $(G_4S)_3$ linker, connects the $V_H$ and $V_L$ in the antigenic scFv.

4. The homodimeric protein according to any one of embodiments 1-3, wherein the antigenic scFv is derived from a monoclonal Ig produced by myeloma or lymphoma cells.

5. The homodimeric protein according to embodiment 1, wherein the antigenic unit is a telomerase, or a functional part thereof.

6. The homodimeric protein according to embodiment 5, wherein said telomerase is hTERT.

7. The homodimeric protein according to embodiment 1, wherein the antigenic unit is derived from a bacterium.

8. The homodimeric protein according to embodiment 7, wherein the bacterium derived antigenic unit is selected from a tuberculosis antigen and a brucellosis antigen.

9. The homodimeric protein according to embodiment 1, wherein the antigenic unit is derived from a virus.

10. The homodimeric protein according to embodiment 9, wherein the virus derived antigenic unit is derived from HIV.

11. The homodimeric protein according to embodiment 10, wherein the HIV derived antigenic unit is derived from gp120 or Gag.

12. The homodimeric protein according to embodiment 9, wherein the antigenic unit is selected from the list consisting of influenza virus hemagglutinin (HA), nucleoprotein, and M2 antigen; and Herpes simplex 2 antigen glycoprotein D.

13. The homodimeric protein according to embodiment 1, wherein the antigenic unit is a cancer associated or a cancer specific antigen.

14. The homodimeric protein according to embodiment 13, wherein the cancer antigenic unit is a melanoma antigen, such as the melanoma antigens tyrosinase, TRP-1 or TRP2.

15. The homodimeric protein according to embodiment 13, wherein the cancer antigenic unit is a prostate cancer antigen, such as the prostate cancer antigen PSA.

16. The homodimeric protein according to embodiment 13, wherein the cancer antigenic unit is a cervix cancer antigen, such as the cervix cancer antigen selected from the list consisting of E1, E2, E4, E6, E7, L1 and L2.

17. The homodimeric protein according to any one of embodiments 1-16, wherein the dimerization motif comprises a hinge region and optionally another domain that facilitate dimerization, such as an immunoglobulin domain, optionally connected through a linker.

18. The homodimeric protein according to embodiment 17, wherein the hinge region is Ig derived, such as derived from IgG3.

19. The homodimeric protein according to any one of embodiments 17-18, wherein the hinge region has the ability to form one, two, or several covalent bonds.

20. The homodimeric protein according to any one of embodiments 17-19, wherein the covalent bond is a disulphide bridge.

21. The homodimeric protein according to any one of embodiments 17-20, wherein the immunoglobulin domain of the dimerization motif is a carboxyterminal C domain, or a sequence that is substantially homologous to said C domain.

22. The homodimeric protein according to embodiment 21, wherein the carboxyterminal C domain is derived from IgG.

23. The homodimeric protein according to any one of embodiments 17-22, wherein the immunoglobulin domain of the dimerization motif has the ability to homodimerize.

24. The homodimeric protein according to any one of embodiments 17-23, wherein said immunoglobulin domain has the ability to homodimerize via noncovalent interactions.

25. The homodimeric protein according to embodiment 24, wherein said noncovalent interactions are hydrophobic interactions.

26. The homodimeric protein according to any one of embodiments 1-25, wherein said dimerization domain does not comprise the CH2 domain.

27. The homodimeric protein according to any one of embodiments 1-26, wherein the dimerization motif consist of hinge exons h1 and h4 connected through a linker to a $C_H3$ domain of human IgG3.

28. The homodimeric protein according to any one of embodiments 17-27, wherein said linker is a $G_3S_2G_3SG$ linker.

29. The homodimeric protein according to any one of embodiments 1-28, wherein said antigenic unit and the dimerization motif is connected through a linker, such as a GLSGL linker.

30. The homodimeric protein according to any one of embodiments 1-29, wherein said targeting unit comprises amino acids 3-70 of SEQ ID NO:1.

31. The homodimeric protein according to any one of embodiments 1-29, wherein said targeting unit consist of amino acids 5-70 of SEQ ID NO:1.

32. The homodimeric protein according to any one of embodiments 1-29, wherein said targeting unit consist of amino acids 3-70 of SEQ ID NO:1.

33. The homodimeric protein according to any one of embodiments 1-30, wherein said targeting unit consist of amino acids 1-70 of SEQ ID NO:1.

34. The homodimeric protein according to any one of embodiments 1-29, which homodimeric protein do not comprise amino acids 1-70 of SEQ ID NO:1.

35. The homodimeric protein according to any one of embodiments 1-29, wherein said targeting unit comprises amino acids 3-70 of SEQ ID NO:2.

36. The homodimeric protein according to any one of embodiments 1-29, wherein said targeting unit consist of amino acids 5-70 of SEQ ID NO:2.

37. The homodimeric protein according to any one of embodiments 1-29, wherein said targeting unit consist of amino acids 3-70 of SEQ ID NO:2.

38. The homodimeric protein according to any one of embodiments 1-29, wherein said targeting unit consist of amino acids 1-70 of SEQ ID NO:2.

39. The homodimeric protein according to any one of embodiments 1-29, which homodimeric protein do not comprise amino acids 1-70 of SEQ ID NO:2.

40. The homodimeric protein according to any one of embodiments 1-32, 35-37, wherein each said targeting unit consist of not more than 68 amino acids, such as 68, 67, or 66 amino acids.

41. The homodimeric protein according to any one of embodiments 1-30, 35, wherein said targeting unit do not contain the amino acid sequence AP at positions 1 and 2 of the targeting unit.

42. The homodimeric protein according to any one of embodiments 1-41, which homodimeric protein have increased affinity for any one chemokine receptor selected from CCR1, CCR3 and CCR5 as compared to the affinity of the same homodimeric protein, wherein the targeting unit consists of amino acids 1-70 of SEQ ID NO:2.

43. A nucleic acid molecule encoding the monomeric protein which can form the homodimeric protein according to any one of embodiments 1-42.

44. The nucleic acid molecule according to embodiment 43 comprised by a vector.

45. The nucleic acid molecule according to embodiments 43 or 44 formulated for administration to a patient to induce production of the homodimeric protein in said patient.

46. The homodimeric protein according to any one of embodiments 1-42 or the nucleic acid molecule according to embodiments 43 or 44 for use as a medicament.

47. A pharmaceutical composition comprising the homodimeric protein according to any one of embodiments 1-42, or the nucleic acid molecule according to embodiments 43 or 44.

48. A host cell comprising the nucleic acid molecule according to embodiments 43 or 44.

49. A method for preparing a homodimeric protein according to any one of embodiments 1-42, the method comprising
 a) transfecting the nucleic acid molecule according to embodiments 43 or 44 into a cell population;
 b) culturing the cell population;
 c) collecting and purifying the homodimeric protein expressed from the cell population.

50. A vaccine against a cancer or an infectious disease comprising an immunologically effective amount of a homodimeric protein according to any one of embodiments 1-42 or nucleic acid molecule according to embodiments 43 or 44 encoding the monomeric protein which can form the homodimeric protein, wherein said vaccine is able to trigger both a T-cell- and B-cell immune response and wherein said homodimeric protein contain an antigenic unit specific for said cancer or infectious disease.

51. The vaccine according to embodiment 50 further comprising a pharmaceutically acceptable carrier and/or adjuvant.

52. The vaccine according to embodiments 50 or 51, wherein said cancer is multiple myeloma or lymphoma, malignant melanoma, HPV induced cancers, prostate cancer, breast cancer, lung cancer, ovarian cancer, and/or liver cancer.

53. The vaccine according to embodiment 50 or 51, wherein said infectious disease is selected from the list consisting of tuberculosis, Influenza, Herpes, CMV, HPV, HBV, HIV, brucellosis, and/or HSV-2.

54. A method of treating a cancer or an infectious disease in a patient, the method comprising administering to the patient in need thereof, a homodimeric protein according to any one of embodiments 1-42, or the nucleic acid molecule according to embodiments 43 or 44 encoding the monomeric protein which can form the homodimeric protein, wherein said homodimeric protein contain an antigen unit specific for said cancer or infectious disease.

Example 1

Mice and Cell Lines

BALB/c mice were obtained from Taconic (Ry, Denmark). Id($\lambda 2^{315}$)-specific T-cell receptor (TCR) transgenic mice have been described (see Bogen B et al. Eur J Immunol 1992 March; 22(3):703-9 and Snodgrass H R et al. Eur J Immunol 1992 August; 22(8):2169-72). The TCR recognizes aa 91-101 of the $\lambda 2^{315}$ light chain, produced by the IgA MOPC315 mouse plasmacytoma, presented on the I-E$^d$ class II molecules. The studies were approved by the National Committee for Animal Experiments (Oslo, Norway). MOPC 315.4 (IgA, $\lambda 2^{315}$), HEK 293 and HEK 293E cells were from ATCC. HEK 293 stably transfected with hCCR5 and hCCR1 were kindly provided by Mario Mellado (Madrid, Spain) and Zack Howard (Frederick, Md.), respectively. HEK 293 stably transfected with Rhesus macaque (GenBank AF005660) were obtained from Pfizer Inc., (Groton, Conn.). The murine lymphoma Esb/MP cells were kindly provided by Jo Van Damme (Leuven, Belgium).

Cloning of Human MIP1a/CCL3 (LD78α or LD78β-Encoding Vaccibodies)

Genes encoding for mature LD78α and LD78β (GenBank NM_002983 and NG_004113, respectively) were amplified from cDNA of CD14-enriched, bone marrow-derived monocytes from a healthy donor. Forward primers (BsmI restriction site, in italic) were:

LD78α:
(SEQ ID NO: 3)
GGTG*TGCATTCCGC*ATCACTTGCTGCTGAC;

LD78β:
(SEQ ID NO: 4)
GGTG*TGCATTCCGC*ACCACTTGCTGCTGAC;

and reverse primer (BsiWI restriction site, in italic) was GACGTACGACTCACCTGCAACTCAGCTCCAGGTC (SEQ ID NO:5). The 68 aa. long (3-70) LD78β-2 was cloned using forward primer (BsmI restriction site, in italic): GGTGTGCATTCCCTTGCTGCTGACACGCC (SEQ ID NO:6).

Point mutated LD78α and LD78β carrying an S instead of a C residue at position 11 were generated by quick change PCR using the following primers: forward CCGACCGCCTCCTGCTTCAG (SEQ ID NO:7) and reverse CTGAAGCAGGAGGCGGTCGG (SEQ ID NO:8). The amplified chemokine genes were inserted into the targeting cassette of vaccibody construct IlhFpLNOH2 (see Fredriksen A B et al. Mol Ther 2006 April; 13(4):776-85) by use of BsmI/BsiWI restriction sites. The resulting vaccibody construct encoded for homodimeric proteins with hCCL3-derived targeting units and MOPC315 scFv in a VH-VL orientation as antigenic unit, connected via a homodimerizing motif consisting of human hinge exons h1 and h4 and CH3 domain of IgG3.

The antigenic unit (scFv$^{315}$) in vaccibodies described above were exchanged with either paired murine Cκ domains (Tunheim G et al. Vaccine 2007 Jun. 11; 25(24): 4723-34) or influenza virus hemagglutinin (HA) from H1N1 A/Puerto Rico/8/34 (Mt. Sinai) (G. Grødeland, manuscript in preparation).

Assessment of Vaccine Protein Production

Supernatants of transiently transfected 293E cells were tested in the following ELISAs. scFv$^{315}$ vaccibodies: DNP-BSA (binds to M315) as coat and biotinylated monoclonal HP6017 (anti-CH3 dimerization motif) for detection; HA vaccibodies: MCA878G (anti-CH3 dimerization motif) as coat and anti-HA biotinylated mAB H36-4-52 for detection; mouse CκCκ vaccibodies: 187.1 mAb (binds to mouse Cκ) as coat and biotinylated 187.1 for detection.

Production, Purification, Quantitation and Proteomic Characterization of Vaccibody Proteins Vaccibody proteins having scFv$^{315}$ as antigenic unit were affinity purified from supernatants of stably transfected NS0 cells on DNP (bound by M315) Sepharose columns. Purified proteins were loaded onto a 4-20% Tris-glycine gel. Following membrane transfer, proteins were detected with either biotinylated HP6017 or Ab2-1.4 (binds to M315) mAbs followed by streptavidin HRP. Vaccibody proteins were quantified by Bradford and ELISA using BSA and mCCL3 vaccibody (see Fredriksen A B et al. Mol Ther 2006 April; 13(4):776-85) as standards, respectively. Protein bands corresponding to LD78β and LD78β-2 vaccibodies with Fv$^{315}$ were excised from a Coomassie-stained polyacrylamide gel and subjected to tryptic in-gel digestion as previously described.

Binding to Human and Murine CCR5 and CCR1

Vaccibody proteins at concentrations ranging from 0.2 to 25 μg/mL were used to stain parental or stably transfected HEK 293 cells or BALB/c splenocytes (gated by FSC/SSC and on CD11b+ CD3− cells). Bound vaccibody proteins were detected by biotinylated HP6017 (binds to CH3 of hIgG3) or Ab2-1.4 (binds to M315) mAbs followed by streptavidin PE. Cells were analyzed on a FACScalibur.

Chemotaxis Assay

Cell migration in vitro was assessed by a 24-well transwell plate (Corning) as previously described. Either 8 μm or 5 μm pore polycarbonate membranes were used for HEK 293 cells and Esb/MP, respectively. Recombinant chemokines were from Peprotech. The results (mean±SE of duplicate samples) are presented as chemotactic index, defined as the fold increase in the number of migrating cells in the presence of chemotactic factors over the spontaneous cell migration (i.e., in the presence of medium alone).

T Cell Stimulation Assays

BALB/c splenocytes were irradiated (8 Gy) and mixed with vaccibody proteins containing scFv$^{315}$ at concentration ranging from 20 to 0.04 μg/mL before addition of in vitro polarized Id$^{315}$-specific Th2 cells derived from TCR-transgenic mice. An Id peptide corresponding to sequence 89-107 of $\lambda 2^{315}$ was used as a positive control.

Human PBMC from three different DR4*01 healthy donors were mixed with supernatants from transiently transfected 293E cells, containing vaccibody proteins with mouse CκCκ as antigenic unit, before irradiation (20 Gy) and addition of T18 T cell clone that recognizes aa. 40-48 of murine Cκ presented by DR4*01. After 48 hrs plates were pulsed with $^3$H-thymidine for 24 hrs before harvesting.

Mouse Immunizations

Vaccibody DNA was purified using Endofree-mega plasmid purification system (Qiagen). 25 μL solution of 0.5 mg/mL vaccibody DNA in sterile 0.9% NaCl was injected intradermally in the lower back of mice, on both sides, followed by electroporation using Dermavax (Cytopulse, Sweden). Groups consisted of 3 to 7 mice.

Anti-Id315 Antibodies Measurement

Mice were bled three, four and six weeks following a single immunization. Myeloma protein M315 (IgA, λ2) was used as coat and anti-Id$^{315}$ Abs in mouse sera were detected by biotinylated anti-mouse IgG1$^a$ or anti-mouse IgG2a$^a$ (BD Pharmingen). Endpoint titers were calculated.

Elispot Assay

Millipore Multiscreen plates (Millipore, Billerca, Mass., USA) were coated with anti-mouse IFNγ (AN18) (12 μg/ml) and then blocked for 2 h with RPMI-1640 (Invitrogen, NY, USA) containing 10% FCS. Single cell splenocytes were prepared individually from mice DNA-vaccinated 3 weeks earlier with HA-containing vaccibodies or NaCl, and incubated overnight at $10^6$, $5 \times 10^5$ and $2.5 \times 10^5$ cells/well with one of the following HA-derived peptides from ProImmune (Oxford, UK): SVSSFERFEIPK (aa. 107-119, I-E$^d$-restricted), HNTNGVTAACSHEG (aa. 126-138, I-A$^d$-restricted) or IYSTVASSL (aa. 633-641, K$^d$ restricted). Plates were washed in PBS and adherent cells lysed by a five minute incubation in de-ionized water prior to incubation with biotinylated anti-mouse IFNγ (1 μg/ml) (XMG1.2, Pharmingen) and Streptavidine alkaline phosphatase conjugate (1:3000) (GE Healthcare, Little Chalfont Buckinghamshire, UK). IFNγ-producing cells were detected by using the BCIP/NBT kit (Zymed Laboratories Inc, Carlsbad, Calif., USA), and counting was performed with KS EliSpot version 4.3.56 from Zeiss on a Zeiss Axioplan 2 imaging system (objective: Epiplan-Neofluar 5x, 442320).

Vaccination of Mice with Vaccibody-HA Constructs.

Mice were anesthetized, shaved, and vaccinated intradermally with 25 μl DNA (0.5 mg/ml) on each side of the lower back region immediately followed by skin electroporation (DermaVax/CytoPulse). 14 days later, the mice were anesthetized with hypnorm/dormicum and challenged with 20 μl influenza (A/Puerto Rico/8/34 (Mt. Sinai) virus (5×LD50). Following challenge, the mice were weighed and closely monitored for clinical signs.

Construction and Expression of Human CCL3-Based Vaccibodies

Homodimeric vaccibodies were constructed that have various hCCL3-based targeting units, a human Ig-derived homodimerization unit and various antigenic units, as indicated in FIG. 1A. The NH$_2$ terminal aa. sequence of the employed LD78α, LD78β, LD78β-2 and the putative effect of the C11S point mutation on chemokine structure LD78β (C11S) are shown in FIG. 1B and 1C, respectively. All vaccibodies were expressed at comparable levels by transiently transfected 293E cells, except LD78β-2 vaccibodies which were consistently expressed to a lower extent (FIG. 2A-C).

The integrity of the vaccibody proteins having scFv$^{315}$ as antigenic unit was tested by SDS-PAGE, where single bands of about 110 kDa were visible that, following membrane blotting, could be stained with appropriate mAbs (FIG. 2D and data not shown for other constructs). The apparently increased size of the mutated (C11S) vaccibody is likely due to an increase in Stokes radius due to abrogation of a S—S bond (FIG. 1C). Under reducing conditions, single bands of about 55 kDA, corresponding to monomers were observed, as would be expected (data not shown).

The NH$_2$ terminal aa. sequence of LD78β vaccibody proteins was further ascertained since NS0 cells or fetal bovine serum in culture medium could have CD26 activity resulting in posttranslational modification of LD78β. Analysis of tryptic digests of LD78β IhF and LD78β-2IhF vaccibody proteins by MALDI-TOF mass spectrometry showed exclusively signals at m/z 1988.89 and m/z 1820.78, corresponding to the N-terminal peptides APLAADTPTACCF-SYTSR (SEQ ID NO:9) and LAADTPTACCFSYTSR (SEQ ID NO: 10), respectively (data not shown). Thus, pure full lenght LD78β or NH$_2$-truncated LD78β-2 vaccibodies can be expressed and purified from stably transfected NS0 cells.

LD78β Vaccibodies and NH$_2$-Truncated Version Bind Human and Murine Chemokine Receptors Given the variability in CCR5 expression between individuals, HEK 293 stably transfected with hCCR5, rather than PBMC, were used for functional studies. LD78β and LD78β-2 vaccibody, but not their point mutated counterpart, bound hCCR5-transfected HEK 293 cells (FIG. 3A, B and data not shown). NH2-truncated LD78β-2 vaccibody displayed stronger binding than full lenght LD78β vaccibody. Point mutated LD78β (C11S) vaccibody did not bind hCCR5-transfected cells (FIG. 3A). LD78β-2, but not LD78β vaccibodies, also bound hCCR1-expressing HEK 293 (FIG. 3C, D and data not shown), which is in agreement with previous reports. There was no staining of parental, untransfected HEK 293 cells (not shown).

LD78β vaccibody, but not its point mutated counterpart, bound CD11b+ BALB/c splenocytes (FIG. 4A), and induced chemotaxis of Esb/MP cells (FIG. 4B), thus providing the rationale for testing LD78β-expressing vaccibodies in mice.

Delivery of Antigen to APC Via Chemokine Receptors Improves T-Cell Responses in Vitro in Mouse and Human Systems BALB/c splenocytes mixed with LD78β vaccibodies that express scFv$^{315}$ antigenic unit induced proliferation of Id$^{315}$-specific Th2 cells from TCR transgenic mice (FIG. 5A). Similar vaccibodies where the C11S mutation had been introduced had a ~100 fold decreased ability to stimulate T cells. When comparing equimolar concentrations of LD78β Vaccibody and an Id peptide encompassing the CDR3 mutations, the Vaccibody was found to be up to 30 times more effective than the peptide at loading the APCs for antigen presentation (not shown).

As for human T cell responses, LD78β vaccibodies that express murine CκCκ as a model antigen were mixed with donor PBMCs and cloned T18 CD4+ T cells that recognize aa 40-48 of murine Cκ in the context of DR4*01. The difference between wild type and point mutated LD78β was less pronounced than in the mouse system (FIG. 5B). Furthermore, targeted antigen delivery is demonstrated by superiority of LD78μ over non-targeted NIP-specific vaccibody (FIG. 5B). Importantly, LD78β-2 vaccibodies outperformed LD78β vaccibodies. Similar results were obtained using three different donors (not shown).

Improved Anti-Id Humoral Response Induced in Mice by LD78β Vaccibodies Containing scFv$^{315}$ The V$_H$+V$_L$ Id of M315 myeloma protein is a very weak self antigen, in fact an extensive immunization scheme including multiple immunizations with complete and incomplete Freund's adjuvant was required to detect anti-Id antibodies. We therefore tested if mice injected intradermally with LD78βscFv315 vaccibody DNA, combined with electroporation, developed anti-Id antibodies. Anti-Id[315] IgG1 (FIG. 6A) and IgG2a (FIG. 6B) responses were detected in mice that had been immunized with LD78β-encoding vaccibodies, further demonstrating that conformational integrity of scFv[315] is maintained in LD78β vaccibody (FIG. 6). IgG1 responses were recorded to a significantly lesser extent in mice receiving the C11S point-mutated vaccibody, whereas the difference for IgG2a was not significant. Furthermore, statistically significant lower Ab responses were observed for both IgG1 and IgG2a in mice that had been immunized with non targeted control vaccibodies (anti-NIP). These result overall suggest that targeted antigen delivery improves antibody responses to a weak self model tumor antigen.

Induction of Influenza Hemagglutinin-Specific CD4+ and CD8+ T-Cell Responses in Mice Following Vaccibody Administration Induction of CD8+ T cell responses was investigated in an influenza model where hemagglutinin (HA) served as the target antigen. HA from strain A/Puerto Rico/8/34 (Mt. Sinai) (H1N1) is known to express three epitopes to which BALB/c mice (H-$2^d$) respond. Two of these are MHC class II-restricted, SVSSFERFEIPK (SEQ ID NO:11) (aa. 107-119) restricted by I-E$^d$ and HNTNGVTAACSHEG (SEQ ID NO:12) (aa. 126-138) restricted by I-A$^d$, respectively. The third epitope, IYSTVASSL (SEQ ID NO:13) (aa. 633-641), is MHC class I-restricted (K$^d$). Following a single intradermal LD78β vaccibody DNA immunization and electroporation, significantly increased IFNγ responses to the class I epitope were observed for targeted vs. non-targeted (C11S) vaccibodies and sham immunization (NaCl) (FIG. 7A). Responses to class II epitopes were slightly elevated but the effect of targeting was not significant (only one immunization was delivered in the present experiments) (FIG. 7A).

LD78β Vaccibody Binds to Rhesus Macaque CCR5

CCR5 is conserved across different species, including monkey. Human and macaque CCR5 genes have very close aa. homology (98%). Like humans, macaques have two CCL3 isoforms. LD78β and LD78β-2 vaccibodies bound in a dose-dependent fashion Rhesus macaque CCR5-expressing HEK 293 cells, whereas the C11S point mutated LD78β did not bind the same cells (FIG. 8, and data not shown). This result indicates that vaccibodies with LD78β and LD78β-2 intended for human use not only can be tested in mice, as above, but also in Rhesus macaques, prior to any human application.

LD78β-HA Vaccibody but not LD78β-2-HA Vaccibody Protects Mice from Influenza.

As shown in FIG. 9, mice were vaccinated with either of the two forms of LD78β, LD78β or LD78β-2. The full length version of LD78β was shown to have superior effect in terms of protecting mice from influenza infection.

SEQUENCES:

LD78β (SEQ ID NO: 1):
APLAADTPTACCFSYTSRQIPQNFIADYFETSSQCSKPSVIFLTKRGRQV
CADPSEEWVQKYVSDLELSA

LD78α (SEQ ID NO: 2):
ASLAADTPTACCFSYTSRQIPQNFIADYFETSSQCSKPGVIFLTKRSRQV
CADPSEEWVQKYVSDLELSA

Items

1. A homodimeric protein of two identical amino acid chains, each amino acid chain comprising a targeting unit comprising an amino acid sequence having at least 80% sequence identity to the amino acid sequence 5-70 of SEQ ID NO:1, and an antigenic unit, the targeting unit and the antigenic unit being connected through a dimerization motif.

2. The homodimeric protein according to item 1, wherein said targeting unit comprises amino acids 3-70 of SEQ ID NO:1.

3. The homodimeric protein according to items 1 or 2, wherein said targeting unit consist of amino acids 5-70 of SEQ ID NO:1.

4. The homodimeric protein according to any one of items 1-3, wherein said targeting unit consist of amino acids 3-70 of SEQ ID NO:1.

5. The homodimeric protein according to any one of items 1-4, wherein said targeting unit consist of amino acids 1-70 of SEQ ID NO:1.

6. The homodimeric protein according to any one of items 1-5, wherein the antigenic unit is an antigenic scFv.

7. The homodimeric protein according to any one of items 1-6, wherein a linker, such as a $(G_4S)_3$ linker, connects the $V_H$ and $V_L$ in the antigenic scFv.

8. The homodimeric protein according to any one of items 1-7, wherein the antigenic scFv is derived from a monoclonal Ig produced by myeloma or lymphoma cells.

9. The homodimeric protein according to any one of items 1-5, wherein the antigenic unit is a telomerase, or a functional part thereof.

10. The homodimeric protein according to item 9, wherein said telomerase is hTERT.

11. The homodimeric protein according to any one of item 1-5, wherein the antigenic unit is derived from a bacterium.

12. The homodimeric protein according to item 11, wherein the bacterium derived antigenic unit is selected from a tuberculosis antigen and a brucellosis antigen.

13. The homodimeric protein according to any one of items 1-5, wherein the antigenic unit is derived from a virus.

14. The homodimeric protein according to item 13, wherein the virus derived antigenic unit is derived from HIV.

15. The homodimeric protein according to item 14, wherein the HIV derived antigenic unit is derived from gp120 or Gag.

16. The homodimeric protein according to item 13, wherein the antigenic unit is selected from the list consisting of influenza virus hemagglutinin (HA), nucleoprotein, M2 antigen; Herpes simplex 2 antigen glycoprotein D; and a Human Papilloma virus antigen, such as any one selected from the list consisting of E1, E2, E6, E7, L1 and L2.

17. The homodimeric protein according to any one of items 1-5, wherein the antigenic unit is a cancer associated or a cancer specific antigen.

18. The homodimeric protein according to item 17, wherein the cancer antigenic unit is a melanoma antigen, such as the melanoma antigens tyrosinase, TRP-1 or TRP2.

19. The homodimeric protein according to item 17, wherein the cancer antigenic unit is a prostate cancer antigen, such as the prostate cancer antigen PSA.

20. The homodimeric protein according to item 17, wherein the cancer antigenic unit is from human papilloma virus, such as the cervix cancer antigen selected from the list consisting of E1, E2, E4, E6 and E7.

21. The homodimeric protein according to any one of items 1-20, wherein the dimerization motif comprises a hinge region and optionally another domain that facilitate dimerization, such as an immunoglobulin domain, optionally connected through a linker.

22. The homodimeric protein according to item 21, wherein the hinge region is Ig derived, such as derived from IgG3.

23. The homodimeric protein according to any one of items 21-22, wherein the hinge region has the ability to form one, two, or several covalent bonds.

24. The homodimeric protein according to any one of items 21-23, wherein the covalent bond is a disulphide bridge.

25. The homodimeric protein according to any one of items 21-24, wherein the immunoglobulin domain of the dimerization motif is a carboxyterminal C domain, or a sequence that is substantially homologous to said C domain.

26. The homodimeric protein according to item 25, wherein the carboxyterminal C domain is derived from IgG.

27. The homodimeric protein according to any one of items 21-26, wherein the immunoglobulin domain of the dimerization motif has the ability to homodimerize.

28. The homodimeric protein according to any one of items 21-27, wherein said immunoglobulin domain has the ability to homodimerize via noncovalent interactions.

29. The homodimeric protein according to item 28, wherein said noncovalent interactions are hydrophobic interactions.

30. The homodimeric protein according to any one of items 1-29, wherein said dimerization domain does not comprise the CH2 domain.

31. The homodimeric protein according to any one of items 1-30, wherein the dimerization motif consist of hinge exons h1 and h4 connected through a linker to a CH3 domain of human IgG3.

32. The homodimeric protein according to any one of items 21-31, wherein said linker is a $G_3S_2G_3SG$ linker.

33. The homodimeric protein according to any one of items 1-32, wherein said antigenic unit and the dimerization motif is connected through a linker, such as a GLSGL linker.

34. The homodimeric protein according to any one of items 1-33, which homodimeric protein do not comprise amino acids 1-70 of SEQ ID NO:1.

35. The homodimeric protein according to any one of items 1-33, wherein said targeting unit comprises amino acids 3-70 of SEQ ID NO:2.

36. The homodimeric protein according to any one of items 1-33, wherein said targeting unit consist of amino acids 5-70 of SEQ ID NO:2.

37. The homodimeric protein according to any one of items 1-33, wherein said targeting unit consist of amino acids 3-70 of SEQ ID NO:2.

38. The homodimeric protein according to any one of items 1-33, wherein said targeting unit consist of amino acids 1-70 of SEQ ID NO:2.

39. The homodimeric protein according to any one of items 1-33, which homodimeric protein do not comprise amino acids 1-70 of SEQ ID NO:2.

40. The homodimeric protein according to any one of items 1-4, 6-37, 39, wherein each said targeting unit consist of not more than 68 amino acids, such as 68, 67, or 66 amino acids.

41. The homodimeric protein according to any one of items 1-4, 6-37, 39-40, wherein said targeting unit do not contain the amino acid sequence AP at positions 1 and 2 of the targeting unit.

42. The homodimeric protein according to any one of items 1-41, which is a first homodimeric protein having increased affinity as compared to the affinity of a second homodimeric protein, which second homodimeric protein only differs from said first homodimeric protein by having a targeting unit, which consists of amino acids 1-70 of SEQ ID NO:2; the increased affinity being for any one chemokine receptor selected from CCR1, CCR3 and CCR5.

43. A nucleic acid molecule encoding the monomeric protein which can form the homodimeric protein according to any one of items 1-42.

44. The nucleic acid molecule according to item 43 comprised by a vector.

45. The nucleic acid molecule according to items 43 or 44 formulated for administration to a patient to induce production of the homodimeric protein in said patient.

46. The homodimeric protein according to any one of items 1-42 or the nucleic acid molecule according to items 43 or 44 for use as a medicament.

47. A pharmaceutical composition comprising the homodimeric protein according to any one of items 1-42, or the nucleic acid molecule according to items 43 or 44.

48. A host cell comprising the nucleic acid molecule according to items 43 or 44.

49. A method for preparing a homodimeric protein according to any one of items 1-42, the method comprising a) transfecting the nucleic acid molecule according to items 43 or 44 into a cell population;

b) culturing the cell population;

c) collecting and purifying the homodimeric protein expressed from the cell population.

50. A vaccine against a cancer or an infectious disease comprising an immunologically effective amount of a homodimeric protein according to any one of items 1-42 or nucleic acid molecule according to items 43 or 44 encoding the monomeric protein which can form the homodimeric protein, wherein said vaccine is able to trigger both a T-cell- and B-cell immune response and wherein said homodimeric protein contain an antigenic unit specific for said cancer or infectious disease.

51. The vaccine according to item 50 further comprising a pharmaceutically acceptable carrier and/or adjuvant.

52. The vaccine according to items 50 or 51, wherein said cancer is multiple myeloma or lymphoma, malignant melanoma, HPV induced cancers, prostate cancer, breast cancer, lung cancer, ovarian cancer, and/or liver cancer.

53. The vaccine according to item 50 or 51, wherein said infectious disease is selected from the list consisting of tuberculosis, Influenza, Herpes, CMV, HPV, HBV, HIV, brucellosis, and/or HSV-2.

54. A method of treating a cancer or an infectious disease in a patient, the method comprising administering to the patient in need thereof, a homodimeric protein according to any one of items 1-42, or the nucleic acid molecule according to items 43 or 44 encoding the monomeric protein which can form the homodimeric protein, wherein said homodimeric protein contain an antigen unit specific for said cancer or infectious disease.

The invention claimed is:

1. A method of treating a cancer or an infectious disease in a patient in need thereof, the method comprising administering to the patient in need thereof a nucleic acid molecule encoding a monomeric protein which can form a homodimeric protein of two identical amino acid chains, each amino acid chain comprising a targeting unit comprising an amino acid sequence having at least 98% sequence identity to the amino acid sequence set forth in positions 5-70 of SEQ ID NO:1, and an antigenic unit specific for said cancer or said infectious disease, the targeting unit and the antigenic unit being connected through a dimerization motif, wherein said homodimeric protein provides MHC class I cross-presentation to CD8+ T cells, and is capable of eliciting an immune response against said antigenic unit.

2. The method of claim 1, wherein said administration is intradermal or intramuscular injection.

3. The method of claim 2, wherein said administration further comprises electroporation.

4. The method of claim 1, wherein said nucleic acid molecule is comprised in a vector.

5. The method of claim 1, wherein said infectious disease is selected from the list consisting of influenza, Herpes, CMV, HPV, HBV, brucellosis, HIV, HSV-2 and tuberculosis.

6. The method of claim 1, wherein the antigenic unit is derived from a bacterium, from a virus, from a HIV antigen or from a HPV antigen.

7. The method of claim 1, wherein the antigenic unit is selected from:
  a. a bacterial antigen selected from the list consisting of a tuberculosis antigen and a brucellosis antigen;
  b. a viral antigen selected from the list consisting of influenza virus hemagglutinin (HA), nucleoprotein, M2 antigen and Herpes simplex 2 antigen glycoprotein D;
  c. a HIV antigen selected from the list consisting of gp120 and Gag; and
  d. a Human Papilloma virus antigen selected from the list consisting of E1, E2, E6, E7, L1 and L2.

8. The method of claim 1, wherein the cancer is selected from the group consisting of multiple myeloma or lymphoma, malignant melanoma, HPV induced cancers, prostate cancer, breast cancer, lung cancer, ovarian cancer, and liver cancer.

9. The method of claim 1, wherein said antigenic unit comprises a cancer associated antigen or a cancer specific antigen.

10. The method of claim 9, wherein said cancer associated antigen is overexpressed on the surface of a cancer cell.

11. The method of claim 9, wherein said cancer associated or cancer specific antigen is selected from the group consisting of melanoma antigen, prostate cancer antigen, HPV antigen, cervix cancer antigen and idiotypic antigen.

12. The method of claim 9, wherein said cancer associated or cancer specific antigen is a cancer associated or cancer specific antigen selected from:
  a. the telomerase hTERT;
  b. a melanoma antigen selected from the list consisting of tyrosinase, TRP-1, and TRP-2;
  c. the prostate cancer antigen PSA;
  d. a cervix cancer antigen selected from the list consisting of human papilloma virus E1, E2, E4, E6, and E7; and
  e. fragments of antibodies, wherein the fragments are the C-terminal scFv derived from the monoclonal Ig produced by myeloma or lymphoma cells, also called the myeloma/lymphoma M component in patients with B cell lymphoma or multiple myeloma.

13. The method of claim 1, wherein said nucleic acid molecule is a DNA molecule.

14. The method of claim 13, wherein said DNA molecule is comprised in an expression vector.

15. The method of claim 14, wherein administration is intramuscular injection.

16. The method of claim 15, wherein the targeting unit consists of the amino acid sequence set forth in positions 1-70 of SEQ ID NO:1.

17. The method of claim 16, wherein said method is a method of treating a cancer.

18. The method of claim 16, wherein said method is a method of treating an infectious disease.

19. A method of treating a cancer or an infectious disease in a patient in need thereof, the method comprising administering to the patient in need thereof a homodimeric protein of two identical amino acid chains, each amino acid chain comprising a targeting unit comprising an amino acid sequence having at least 98% sequence identity to the amino acid sequence set forth in positions 5-70 of SEQ ID NO: 1, and an antigen unit specific for said cancer or said infectious disease, the targeting unit and the antigenic unit being connected through a dimerization motif, wherein said homodimeric protein provides MHC class I cross-presentation to CD8+ T cells, and is capable of eliciting an immune response against said antigenic unit.

* * * * *

SEQUENCE LISTING

<160> NUMBER OF SEQ ID NOS: 13

<210> SEQ ID NO 1
<211> LENGTH: 70
<212> TYPE: PRT
<213> ORGANISM: Homo sapiens

<400> SEQUENCE: 1

Ala Pro Leu Ala Ala Asp Thr Pro Thr Ala Cys Cys Phe Ser Tyr Thr
1               5                   10                  15

Ser Arg Gln Ile Pro Gln Asn Phe Ile Ala Asp Tyr Phe Glu Thr Ser
            20                  25                  30

Ser Gln Cys Ser Lys Pro Ser Val Ile Phe Leu Thr Lys Arg Gly Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70

<210> SEQ ID NO 2
<211> LENGTH: 70
<212> TYPE: PRT
<213> ORGANISM: Homo sapiens

<400> SEQUENCE: 2

Ala Ser Leu Ala Ala Asp Thr Pro Thr Ala Cys Cys Phe Ser Tyr Thr
1               5                   10                  15

Ser Arg Gln Ile Pro Gln Asn Phe Ile Ala Asp Tyr Phe Glu Thr Ser
            20                  25                  30

Ser Gln Cys Ser Lys Pro Gly Val Ile Phe Leu Thr Lys Arg Ser Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70

<210> SEQ ID NO 3
<211> LENGTH: 30
<212> TYPE: DNA
<213> ORGANISM: Artificial Sequence
<220> FEATURE:
<223> OTHER INFORMATION: DNA primer

<400> SEQUENCE: 3
ggtgtgcatt ccgcatcact tgctgctgac                                    30

<210> SEQ ID NO 4
<211> LENGTH: 30
<212> TYPE: DNA
<213> ORGANISM: Artificial Sequence
<220> FEATURE:
<223> OTHER INFORMATION: DNA primer

<400> SEQUENCE: 4
ggtgtgcatt ccgcaccact tgctgctgac                                    30

<210> SEQ ID NO 5
<211> LENGTH: 34
<212> TYPE: DNA
<213> ORGANISM: Artificial Sequence
<220> FEATURE:
<223> OTHER INFORMATION: DNA primer

```
<400> SEQUENCE: 5
gacgtacgac tcacctgcaa ctcagctcca ggtc                                34

<210> SEQ ID NO 6
<211> LENGTH: 29
<212> TYPE: DNA
<213> ORGANISM: Artificial Sequence
<220> FEATURE:
<223> OTHER INFORMATION: DNA primer

<400> SEQUENCE: 6
ggtgtgcatt cccttgctgc tgacacgcc                                     29

<210> SEQ ID NO 7
<211> LENGTH: 20
<212> TYPE: DNA
<213> ORGANISM: Artificial Sequence
<220> FEATURE:
<223> OTHER INFORMATION: DNA primer

<400> SEQUENCE: 7
ccgaccgcct cctgcttcag                                               20

<210> SEQ ID NO 8
<211> LENGTH: 20
<212> TYPE: DNA
<213> ORGANISM: Artificial Sequence
<220> FEATURE:
<223> OTHER INFORMATION: DNA primer

<400> SEQUENCE: 8
ctgaagcagg aggcggtcgg                                               20

<210> SEQ ID NO 9
<211> LENGTH: 18
<212> TYPE: PRT
<213> ORGANISM: Homo sapiens

<400> SEQUENCE: 9

Ala Pro Leu Ala Ala Asp Thr Pro Thr Ala Cys Cys Phe Ser Tyr Thr
1               5                   10                  15

Ser Arg

<210> SEQ ID NO 10
<211> LENGTH: 16
<212> TYPE: PRT
<213> ORGANISM: Homo sapiens

<400> SEQUENCE: 10

Leu Ala Ala Asp Thr Pro Thr Ala Cys Cys Phe Ser Tyr Thr Ser Arg
1               5                   10                  15

<210> SEQ ID NO 11
<211> LENGTH: 12
<212> TYPE: PRT
<213> ORGANISM: Influenza A virus

<400> SEQUENCE: 11

Ser Val Ser Ser Phe Glu Arg Phe Glu Ile Pro Lys
1               5                   10

<210> SEQ ID NO 12
<211> LENGTH: 14
```

-continued

```
<212> TYPE: PRT
<213> ORGANISM: Influenza A virus

<400> SEQUENCE: 12

His Asn Thr Asn Gly Val Thr Ala Ala Cys Ser His Glu Gly
1               5                   10

<210> SEQ ID NO 13
<211> LENGTH: 9
<212> TYPE: PRT
<213> ORGANISM: Influenza A virus

<400> SEQUENCE: 13

Ile Tyr Ser Thr Val Ala Ser Ser Leu
1               5
```